US011918419B2

United States Patent
Tezuka et al.

(10) Patent No.: US 11,918,419 B2
(45) Date of Patent: Mar. 5, 2024

(54) ULTRASOUND DIAGNOSTIC APPARATUS AND METHOD FOR DIAGNOSING ULTRASOUND PROBE

(71) Applicant: Canon Medical Systems Corporation, Otawara (JP)

(72) Inventors: Kazuo Tezuka, Nasushiobara (JP); Shouichi Nakauchi, Nasushiobara (JP); Yoshinori Goto, Nasushiobara (JP); Naoki Yoneyama, Yaita (JP); Takayuki Gunji, Otawara (JP); Shigemitsu Nakaya, Nasushiobara (JP); Norihisa Kikuchi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 0 days.

(21) Appl. No.: 17/212,042

(22) Filed: Mar. 25, 2021

(65) Prior Publication Data

US 2021/0353258 A1 Nov. 18, 2021

(30) Foreign Application Priority Data

May 15, 2020 (JP) .................. 2020-085953

(51) Int. Cl.
*A61B 8/00* (2006.01)
*A61B 8/08* (2006.01)

(52) U.S. Cl.
CPC .......... *A61B 8/5207* (2013.01); *A61B 8/4245* (2013.01); *A61B 8/44* (2013.01);
(Continued)

(58) Field of Classification Search
CPC ..... A61B 8/5207; A61B 8/4245; A61B 8/461; A61B 8/4477; A61B 8/465; A61B 8/468;
(Continued)

(56) References Cited

U.S. PATENT DOCUMENTS

2006/0052703 A1 3/2006 Kumazawa
2010/0016720 A1 1/2010 Iwasaki
(Continued)

FOREIGN PATENT DOCUMENTS

CN 103284754 A 9/2013
CN 103687546 A 3/2014
(Continued)

OTHER PUBLICATIONS

Weigang B, Moore GW, Gessert J, Phillips WH, Schafer M. The Methods and Effects of Transducer Degradation on Image Quality and the Clinical Efficacy of Diagnostic Sonography. Journal of Diagnostic Medical Sonography. 2003;19(1):3-13. doi:10.1177/8756479302239545 (Year: 2003).*

(Continued)

*Primary Examiner* — Serkan Akar
*Assistant Examiner* — James F McDonald
(74) *Attorney, Agent, or Firm* — Oblon, McClelland, Maier & Neustadt, L.L.P.

(57) ABSTRACT

According to one embodiment, an ultrasound diagnostic apparatus can be connected with an ultrasound probe including a plurality of elements adapted to transmit ultrasound signals and to receive reflected wave signals from a subject or from the air. The ultrasound diagnostic apparatus includes processing circuitry. The processing circuitry diagnoses states of the elements based on a feature value of the reflected wave signal. The processing circuitry also prepares, based on the states, deterioration degree information indicative of the deterioration degrees of the elements. The processing circuitry superimposes the deterioration degree information onto an ultrasound image of the subject and causes a display to display a resultant image.

15 Claims, 11 Drawing Sheets

(52) U.S. Cl.
CPC ............ *A61B 8/4444* (2013.01); *A61B 8/461* (2013.01); *A61B 8/465* (2013.01); *A61B 8/468* (2013.01); *A61B 8/58* (2013.01); *A61B 8/4477* (2013.01); *A61B 8/5292* (2013.01)

(58) Field of Classification Search
CPC ....... A61B 8/5292; A61B 8/44; A61B 8/4444; A61B 90/08; A61B 2090/0804; A61B 8/4483
See application file for complete search history.

(56) References Cited

U.S. PATENT DOCUMENTS

| | | | |
|---|---|---|---|
| 2010/0268503 A1* | 10/2010 | Specht | A61B 8/587 73/1.82 |
| 2013/0194891 A1* | 8/2013 | Kristoffersen | A61B 8/44 367/13 |
| 2014/0043933 A1* | 2/2014 | Belevich | A61B 8/483 367/7 |
| 2014/0126791 A1 | 5/2014 | Iimura et al. | |
| 2017/0290567 A1 | 10/2017 | Fujita | |
| 2020/0000435 A1* | 1/2020 | Anand | A61B 8/46 |
| 2020/0305848 A1 | 10/2020 | Sabata | |

FOREIGN PATENT DOCUMENTS

| | | | |
|---|---|---|---|
| JP | 2002-306478 A | | 10/2002 |
| JP | 2006-95291 A | | 4/2006 |
| JP | 2006-95292 A | | 4/2006 |
| JP | WO 2008/035415 A1 | | 3/2008 |
| JP | 2019-107419 A | | 7/2019 |
| WO | WO 2013/011800 A1 | | 1/2013 |
| WO | WO 2019/124170 A1 | | 6/2019 |

OTHER PUBLICATIONS

Eghbali, Ladan. The impact of defective ultrasound transducers on the evaluation results of ultrasound imaging of blood flow. KTH Technology and Health—Royal Institute of Technology, Stockholm (2014). (Year: 2014).*

Lorentsson R, Hosseini N, Johansson JO, et al. Method for automatic detection of defective ultrasound linear array transducers based on uniformity assessment of clinical images—A case study. J Appl Clin Med Phys. 2018;19(2):265-274. doi:10.1002/acm2.12248 (Year: 2018).*

Gistvik H, Pettersson S. Effects of dead elements in ultrasound transducers. KTH Technology and Health—Royal Institute of Technology, Stockholm (2013). Masters Thesis in Med Engr, GE Healthcare. (Year: 2013).*

Office Action dated Jul. 5, 2023, in Chinese Patent Application No. 202110520845.3 filed May 13, 2021, citing documents 1, 15-17 therein, 9 pages.

Office Action dated Nov. 14, 2023, in corresponding Japanese Patent Application No. 2020-085953, 4 pages.

* cited by examiner

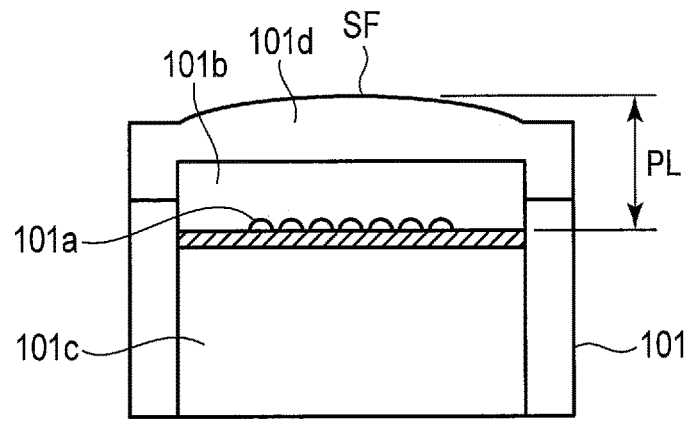
F I G. 2
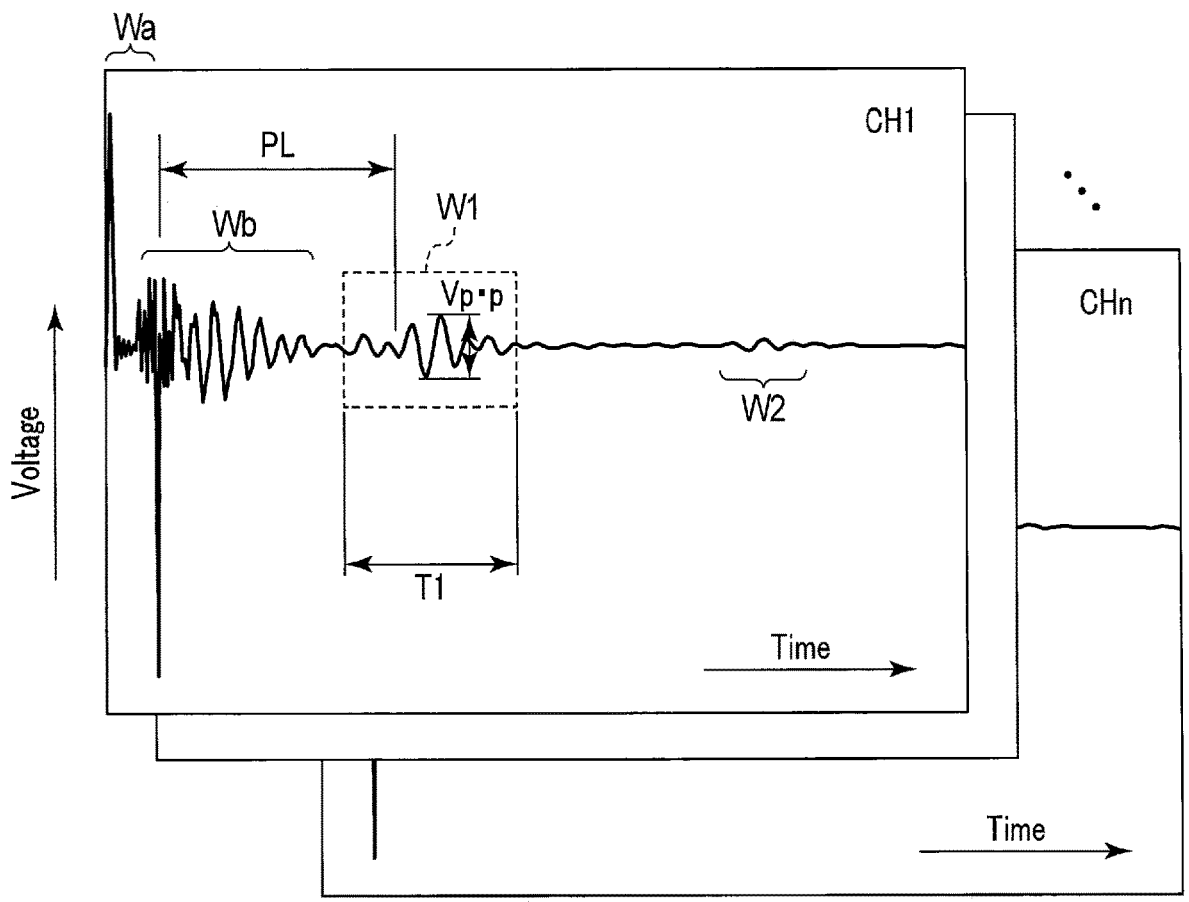
F I G. 3

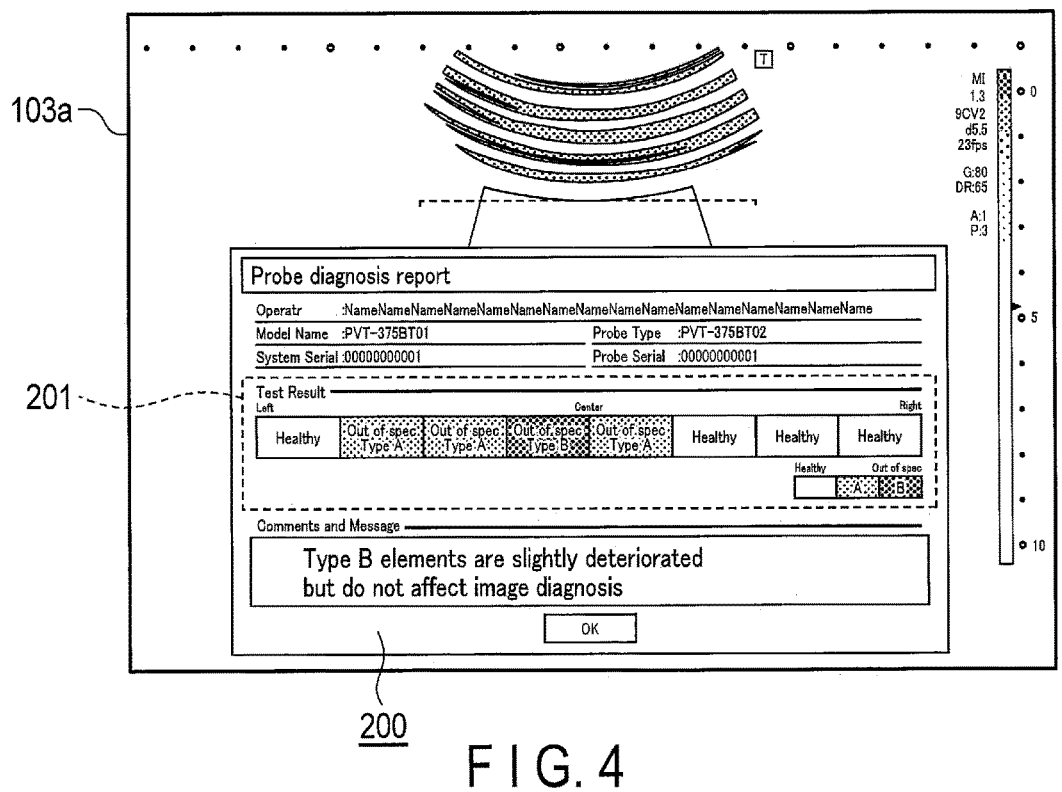

FIG. 4

| Deterioration degree | Comments and messages |
|---|---|
| Healthy | Elements show no deterioration |
| Type A | Type A elements might be deteriorated but do not affect image diagnosis |
| Type B | Type B elements show slight deterioration but image diagnosis is not affected. If more detailed tests are desired, contact the service staff at the nearby office of ABC company |
| Type C | Type C elements are significantly deteriorated and image diagnosis will likely be affected. More detailed tests are recommended. Contact the service staff at the nearby office of ABC company |
| Type D | Type D elements are defective elements and cannot be used in image diagnosis. They must be repaired or replaced. Contact the service staff at the nearby office of ABC company |
| Type E | Type E elements are defective elements and cannot be used in image diagnosis. They must be replaced. Contact the service staff at the nearby office of ABC company |

FIG. 5

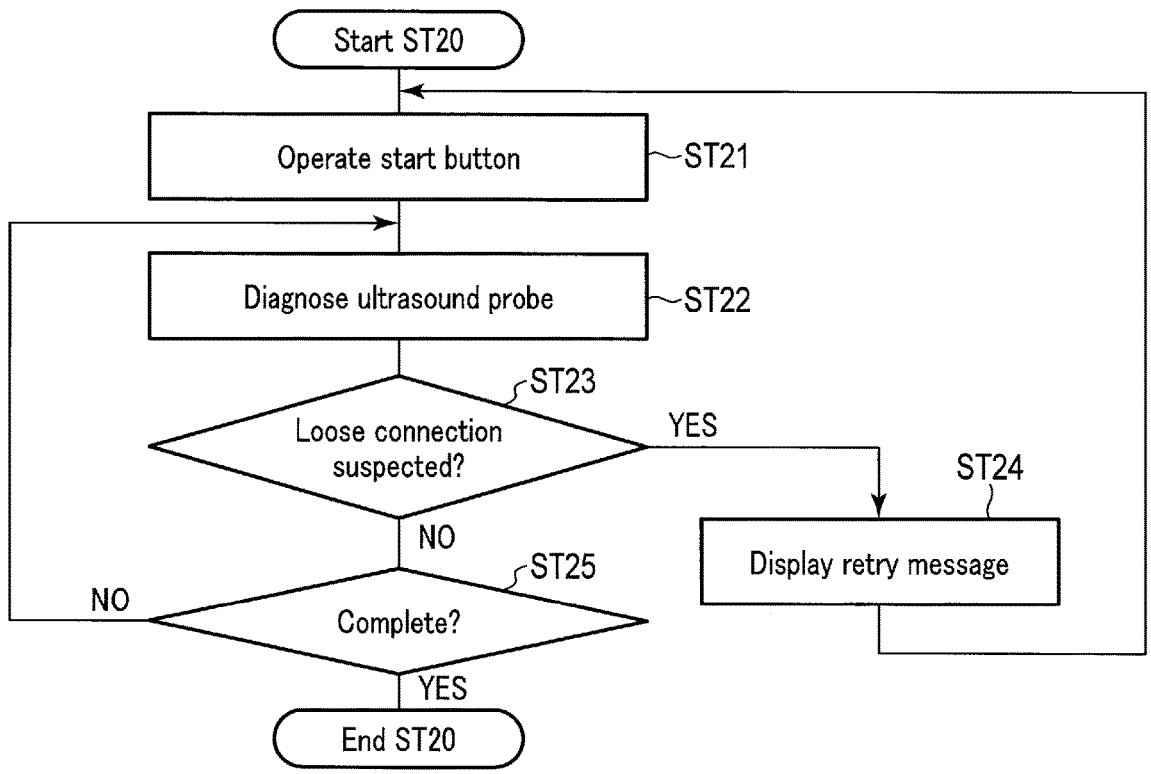
F I G. 8
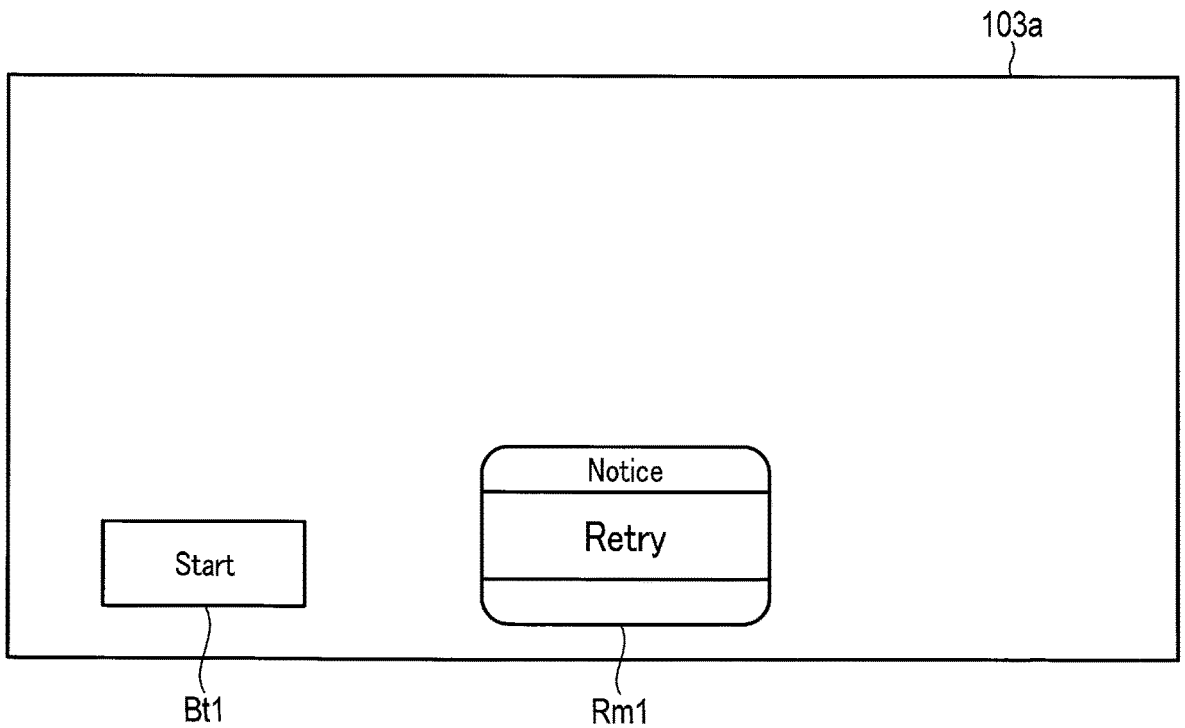
F I G. 9

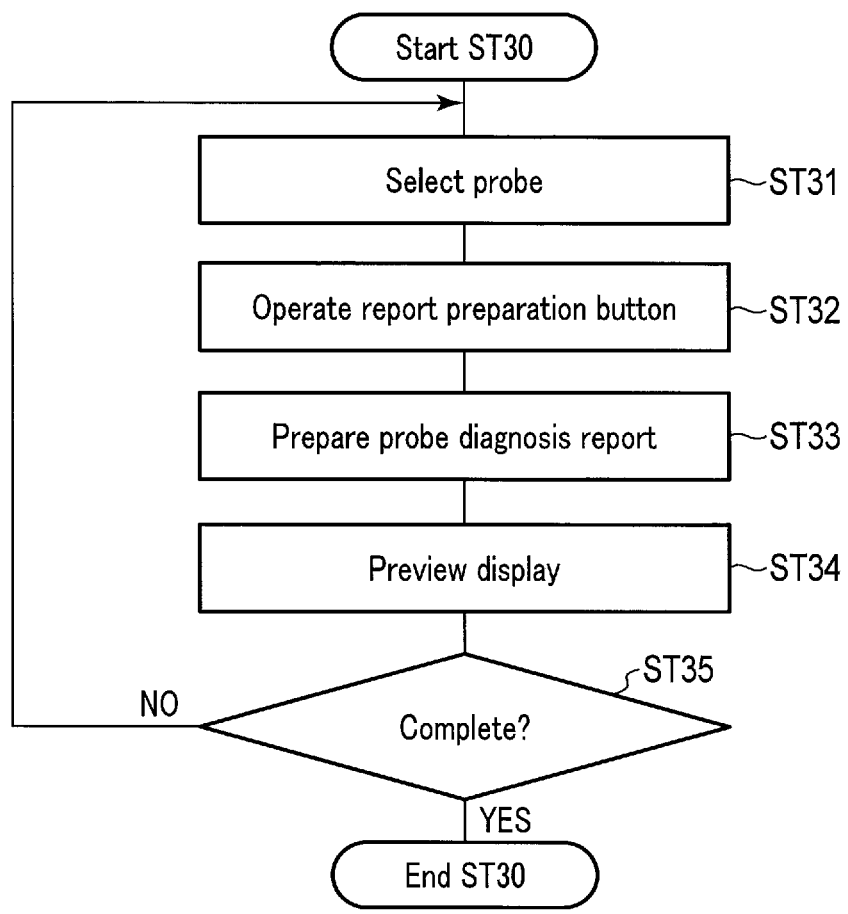
F I G. 10

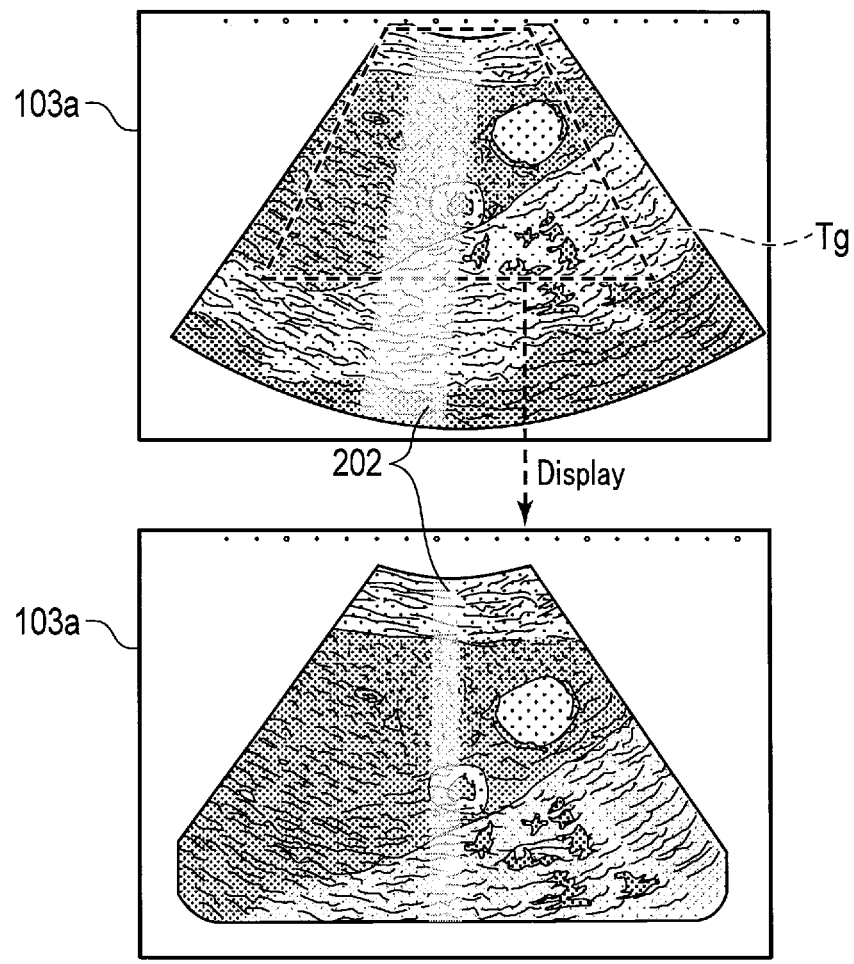
F I G. 12

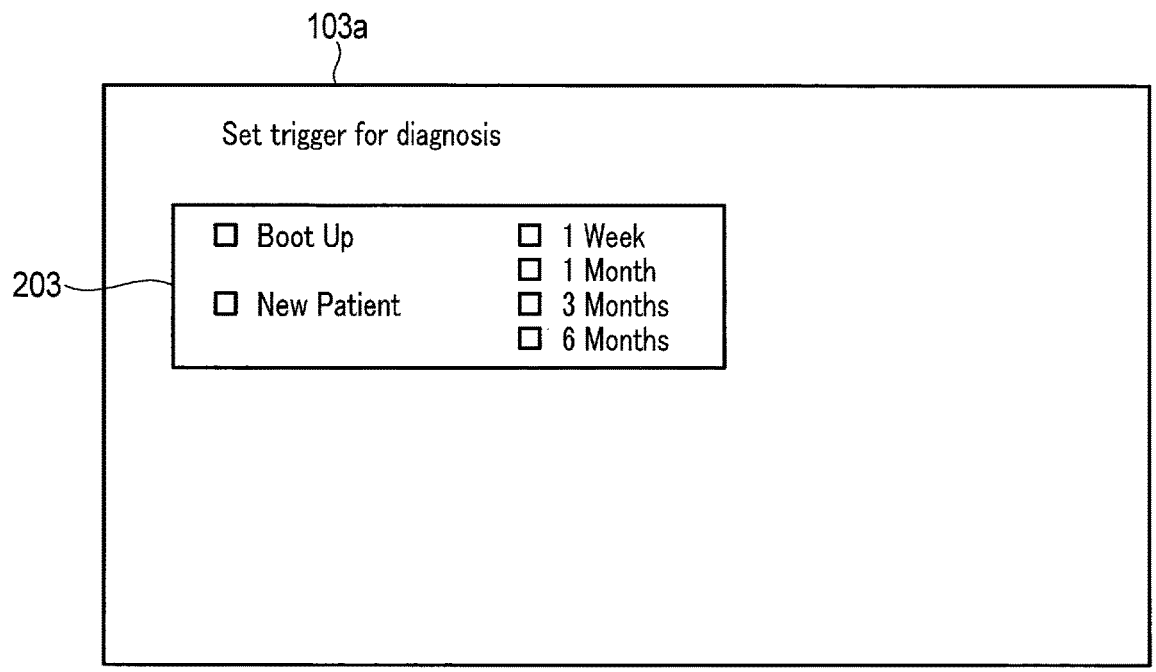
F I G. 15
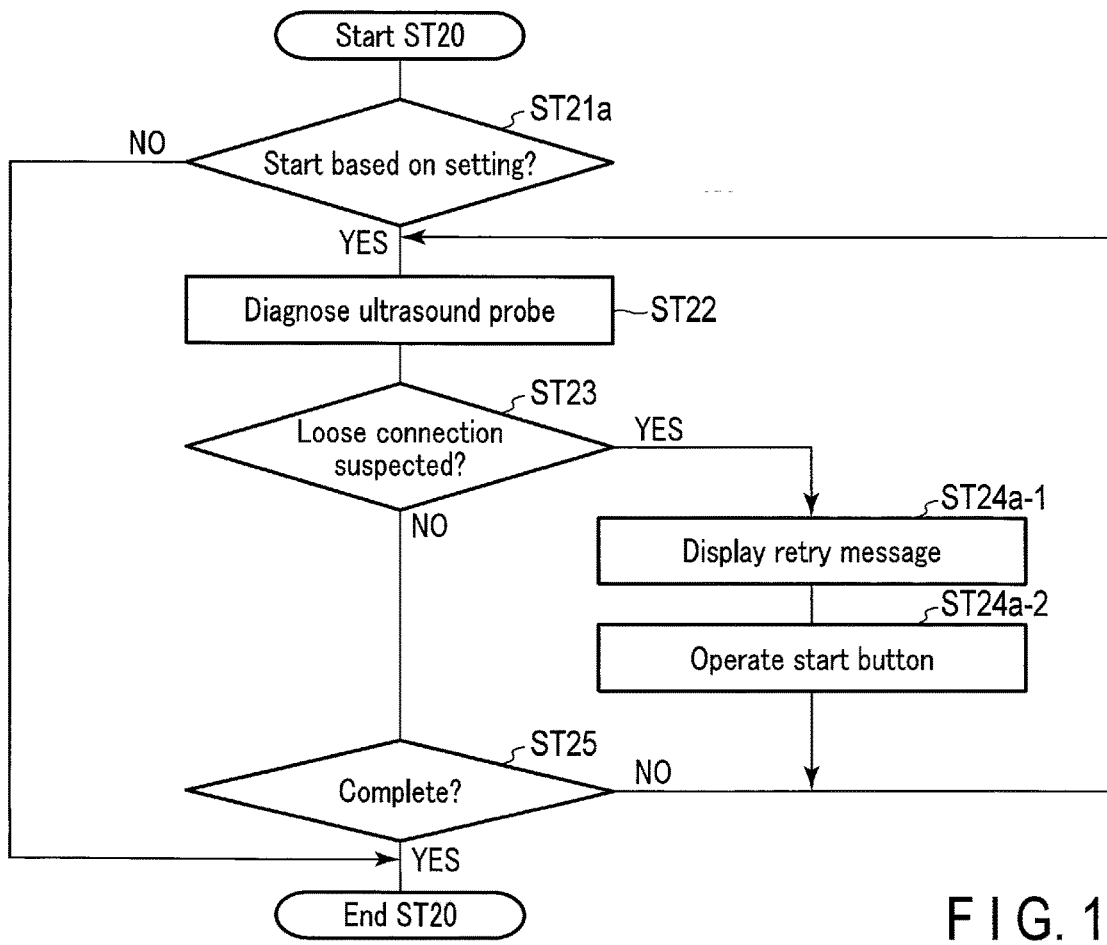
F I G. 16

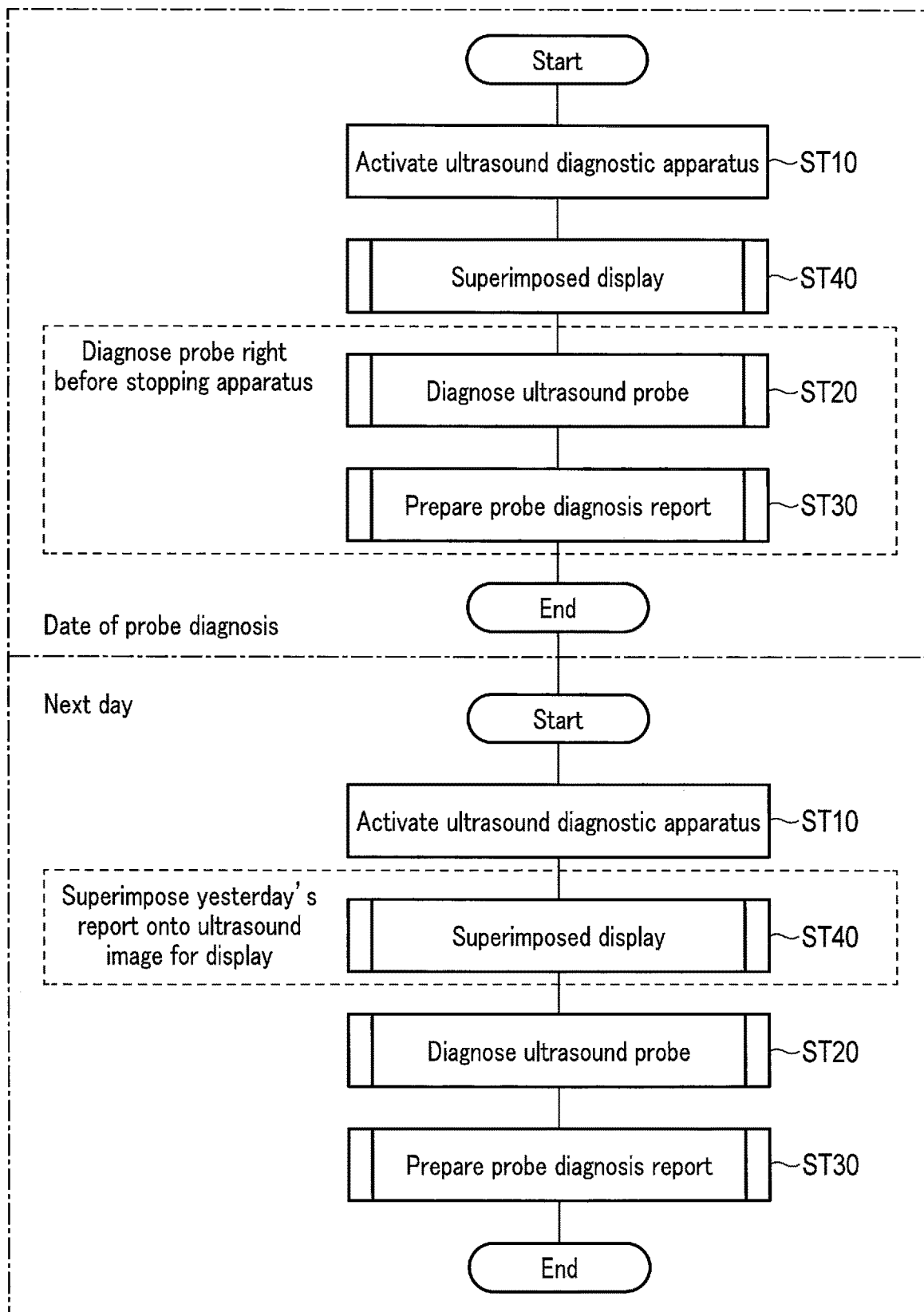
F I G. 17

ULTRASOUND DIAGNOSTIC APPARATUS AND METHOD FOR DIAGNOSING ULTRASOUND PROBE

CROSS-REFERENCE TO RELATED APPLICATION(S)

This application is based upon and claims the benefit of priority from prior Japanese Patent Application No. 2020-85953, filed May 15, 2020, the entire contents of which are incorporated herein by reference.

FIELD

Embodiments described herein relate generally to an ultrasound diagnostic apparatus and a method for diagnosing an ultrasound probe.

BACKGROUND

An ultrasound diagnostic apparatus, as compared to the state at the beginning of use, can suffer from deterioration of components or elements in its ultrasound probe in accordance with how it has been used at the medical site, or due to aging or the like. An ultrasound diagnostic apparatus can also fall into a situation where an unintentional or accidental dropping of the ultrasound probe causes malfunctions of the elements therein. It is not easy to tell the states of elements in the ultrasound probe by appearance, and as such, the ultrasound probe is diagnosed on a regular basis or at random times by a maintenance staff other than a physician or an owner who may use the ultrasound probe. The result of this diagnosis is reported to the physician, the owner, etc., from the maintenance staff.

BRIEF DESCRIPTION OF THE DRAWINGS

FIG. 2 is a sectional view schematically showing an example of the head structure of an ultrasound probe according to the first embodiment.

FIG. 3 is a schematic diagram showing reflected wave signals received by the ultrasound probe according to the first embodiment.

FIG. 4 is a schematic diagram for explaining a probe diagnosis report according to the first embodiment.

FIG. 5 is a schematic diagram for explaining messages appearing in the probe diagnosis report according to the first embodiment.

FIG. 8 is a flowchart for explaining operations in step ST20 according to the first embodiment.

FIG. 9 is a schematic diagram showing one exemplary form of a start button and a retry message, which will be referred to for explaining operations according to the first embodiment.

FIG. 10 is a flowchart for explaining operations in step ST30 according to the first embodiment.

FIG. 12 is a schematic diagram for explaining superimposed display according to a second embodiment.

FIG. 15 is a schematic diagram showing an example of a screen according to a fifth embodiment, which is for setting triggers for the diagnosis of an ultrasound probe.

FIG. 16 is a flowchart for explaining operations according to the fifth embodiment.

FIG. 17 is a flowchart for explaining operations according to a sixth embodiment.

DETAILED DESCRIPTION

According to one embodiment, an ultrasound diagnostic apparatus can be connected with an ultrasound probe including a plurality of elements adapted to transmit ultrasound signals and to receive reflected wave signals from a subject or from the air. The ultrasound diagnostic apparatus generates an ultrasound image based on an output of the elements. The ultrasound diagnostic apparatus includes processing circuitry. The processing circuitry performs a diagnosing process of diagnosing states of the elements based on a feature value of the reflected wave signal. The processing circuitry performs a preparing process of preparing deterioration degree information indicative of the deterioration degrees of the elements based on the diagnosed states. The processing circuitry performs a display controlling process of superimposing the deterioration degree information onto an ultrasound image of the subject and causes a display to display a resultant image.

Embodiments will be described with reference to the drawings. For each embodiment, the description will use the same reference symbols for the same or substantially the same components or features that appear in already discussed drawings. The description will in principle omit details of such components, etc., and concentrate on the portions differing from the preceding explanation.

First Embodiment

The first embodiment relates to a form of displaying the result of a probe check. For example, a probe check is conducted in an ultrasound diagnostic apparatus to prepare a report indicative of the normal or deteriorated states of probe elements and the result of a malfunction check, and this report is displayed on a screen in association with an ultrasound image. Here, the display form is not limited to a report. Examples of the display form include an ultrasound image on which a part corresponding to a deteriorated element or a defective element is superimposed based on the check result. This will be described in more detail with reference to the drawings.

Figure 1:
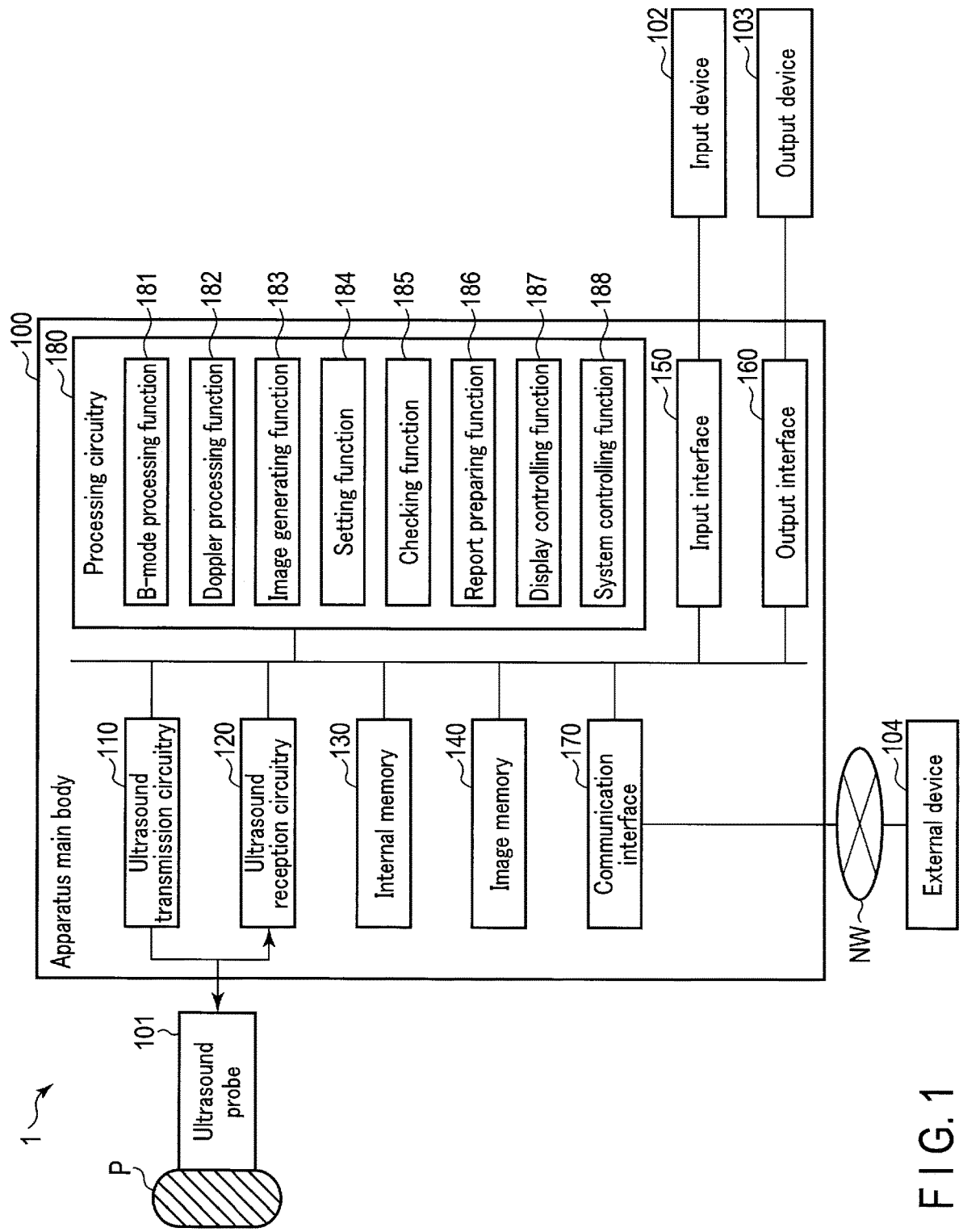
FIG. 1 is a block diagram showing an exemplary configuration of an ultrasound diagnostic apparatus according to a first embodiment.

FIG. 1 is a block diagram showing an exemplary configuration of an ultrasound diagnostic apparatus according to the first embodiment, and FIG. 2 is a sectional view schematically showing an example of the head structure of its ultrasound probe. The ultrasound diagnostic apparatus shown in FIG. 1 is denoted by reference symbol "1" and includes an apparatus main body 100 and an ultrasound probe 101. The apparatus main body 100 is connected to an input device 102 and an output device 103 (e.g., a display, a speaker, etc.). Also, the apparatus main body 100 is connected to an external device 104 via a network NW. An example of the external device 104 is a server or the like, equipped with picture archiving and communication systems (PACS).

The ultrasound probe 101 includes multiple elements adapted to transmit ultrasound signals and to receive reflected wave signals from a subject or from the air. The ultrasound probe 101 is connected to the apparatus main body 100 which is capable of generating ultrasound images based on outputs from the multiple elements. In an exemplary implementation, the ultrasound probe 101 performs ultrasound scanning for a scan region in a subject P, which may be a biological subject (patient), under the control of the apparatus main body 100. As shown in FIG. 2, i.e., the sectional view of the probe head, the ultrasound probe 101 includes, for example, multiple piezoelectric vibrators 101a referred to as the "multiple elements" here, a matching layer 101b provided between the piezoelectric vibrators 101a and the casing, a backing member 101c for preventing ultrasound waves from propagating backwardly against the radiation direction from the piezoelectric vibrators 101a, an acoustic lens 101d provided over the matching layer 101b in the radiation direction, and so on. As the term used herein, "the piezoelectric vibrator" may be replaced by "the element". The ultrasound probe 101 may be, for example, a one-dimensional array linear probe constituted by multiple ultrasound transducers disposed along a predetermined direction. The ultrasound probe 101 can be freely connected to and detached from the apparatus main body 100. The ultrasound probe 101 may include one or more buttons to be pressed down for actions such as offset processing, freezing of an ultrasound image (freeze action), etc.

The multiple piezoelectric vibrators 101a generate ultrasound waves according to drive signals supplied from ultrasound transmit circuitry 110 of the apparatus main body 100, which will be described later. The ultrasound probe 101 accordingly transmits the ultrasound waves to the subject P. The ultrasound waves, upon transmission into the subject P from the ultrasound probe 101, are repeatedly reflected by the discontinuous acoustic-impedance surfaces of the body tissues in the subject P, and are received by the piezoelectric vibrators 101a as reflected wave signals. The received reflected wave signals vary their amplitude depending on the difference in acoustic impedance between the discontinuous surfaces that have reflected the ultrasound waves. When pulses of the transmitted ultrasound waves are reflected by a blood flow or a surface of the cardiac wall, etc. that is in motion, the produced reflected wave signals involve a frequency shift attributable to the Doppler effect according to the moving object's velocity component in the direction of the ultrasound transmission. The ultrasound probe 101 receives the reflected wave signals from the subject P and converts them into electric signals.

When diagnosed, the ultrasound probe 101 performs ultrasound scanning with its head positioned in the air, under the control of the apparatus main body 100. At this time, the ultrasound signals transmitted from the multiple piezoelectric vibrators 101a propagate by a propagation length PL, and are reflected by a boundary face SF between the surface of the acoustic lens 101d and the air. The reflected wave signals constituted by the reflected ultrasound waves then propagate by the propagation length PL and are received by each of the piezoelectric vibrators 101a. The piezoelectric vibrators 101a output the received reflected wave signals to the apparatus main body 100 where ultrasound reception circuitry 120 is provided for the ultrasound probe 101 for reception signals.

FIG. 3 is a schematic diagram showing an example of the reflected wave signals received by the apparatus main body 100 shown in FIG. 1. Note that FIG. 3 shows the reflected wave signals that are produced when drive signals of a drive frequency corresponding to the center frequency of the ultrasound probe 101 are supplied to the piezoelectric vibrators 101a. The reflected wave signals are collected for each channel. The reflected wave signals include a transmission waveform Wa, a multi-reflection unwanted oscillatory waveform Wb, a first reflected wave W1, and a second reflected wave W2. In the context of this embodiment, the first reflected wave W1 refers to an ultrasound wave which, as a reflected wave, has made a round trip between the piezoelectric vibrators 101a and the boundary face SF for the first time. The second reflected wave W2 in the embodiment refers to an ultrasound wave that has made a round trip between the piezoelectric vibrators 101a and the boundary face SF for the second time as a reflected wave. Either the first reflected wave W1 or the second reflected wave W2 may be used as a surface reflected wave for measuring transmission/reception sensitivity. Which of the first reflected wave W1 and the second reflected wave W2 should be used is predetermined for each model of the ultrasound probe 101. The description will assume the instances where the first reflected wave W1 is used. Here, the first reflected wave W1 is acquired by extracting, from the reflected wave signals, a portion that falls within a waveform acquisition interval T1 set in advance. However, the method for acquiring the first reflected wave W1 is not limited to this. For example, the first reflected wave W1 may be acquired by subtracting previously specified probe noise data from the reflected wave signals. In any case, upon acquisition of the first reflected wave W1 of the reflected wave signals, one or more feature values such as an amplitude, a center frequency, a bandwidth, etc. are acquired based on the acquired first reflected wave W1. As one example, in the case of an amplitude, a sensitivity peak value is obtained as the feature value. More specifically, the maximum amplitude value (Vp-p) within the first reflected wave W1 is calculated as the sensitivity peak value. The sensitivity peak value is obtained for each channel (element). The obtained sensitivity peak value is stored as measurement data in an internal memory 130 of the apparatus main body 100. Also, a set of data including the date and time of the transmission/reception sensitivity measurement for the ultrasound probe 101, the temperature in the ultrasound probe 101 during the measurement, the identification information of the ultrasound probe 101, etc. is stored in the internal memory 130 in association with the measurement data. Such measurement data is used for diagnosing the element state. That is, the measurement data obtained at the manufacture of the ultrasound diagnostic apparatus 1 is used as initial data, and the measurement data obtained regularly or at random times is used as diagnosis data. The element state can then be diagnosed based on the difference between the initial data and the diagnosis data of the corresponding element. Also, ranking the differences found for the respective elements allows for the preparation of deterioration degree information indicative of the degrees of deterioration occurring in the respective elements.

Note that what is shown in FIG. 1 is an example that assumes a connection relationship between the ultrasound probe 101 as a single unit and the apparatus main body 100. However, the apparatus main body 100 may be adapted for concurrent connections with multiple ultrasound probes. Which of the connected ultrasound probes should be used in ultrasound scanning can be discretionarily selected by, for example, software buttons appearing on a touch panel.

The apparatus main body 100 is an apparatus adapted to generate ultrasound images based on the reflected wave signals received by the ultrasound probe 101. The apparatus main body 100 includes the ultrasound transmit circuitry 110, the ultrasound reception circuitry 120, and the internal memory 130, which are mentioned above, as well as an image memory 140, an input interface 150, an output interface 160, a communication interface 170, and processing circuitry 180.

The ultrasound transmit circuitry 110 is a processor for supplying drive signals to the ultrasound probe 101. The ultrasound transmit circuitry 110 is realized by, for example, a trigger generating circuit, a delay circuit, a pulser circuit, etc. The trigger generating circuit repeats generation of a rate pulse for forming ultrasound waves for transmission, at a predetermined rate frequency. The delay circuit applies a delay time to each rate pulse generated by the trigger generating circuit. The delay time is intended for the respective piezoelectric vibrator, and required for converging the ultrasound waves output from the ultrasound probe 101 into a beam shape and determining the transmission directivity. The pulser circuit applies the drive signals (drive pulses) to the piezoelectric vibrators in the ultrasound probe 101 at timings according to the rate pulses. By controlling the delay circuit to vary the delay time applied to each rate pulse, it is possible to discretionarily adjust the direction of transmission from the surfaces of the piezoelectric vibrators.

The ultrasound transmit circuitry 110 is also capable of discretionarily changing the output intensity of ultrasound waves by the drive signals. With an increased output intensity, the ultrasound diagnostic apparatus 1 can suppress the influence of the ultrasound waves attenuated within the subject P. When the influence of the ultrasound wave attenuation is reduced, the ultrasound diagnostic apparatus 1 can accordingly acquire reflected wave signals of a large S/N ratio at the reception operation.

In general, an ultrasound wave propagating within a subject P experiences attenuation of its vibration strength (which may also be called acoustic power) corresponding to the output intensity. The attenuation of acoustic power occurs due to absorption, scattering, reflection, etc. How much attenuation occurs in the acoustic power depends on the frequency of ultrasound waves, and the distance in the direction of ultrasound wave radiation. For example, a larger frequency of ultrasound waves produces less attenuation. Also, a longer distance in the direction of ultrasound wave radiation produces larger attenuation.

The ultrasound reception circuitry 120 is a processor for performing various types of processing on the reflected wave signals received by the ultrasound probe 101 to generate reception signals. That is, the ultrasound reception circuitry 120 generates reception signals for the ultrasound reflected wave signals acquired by the ultrasound probe 101. As a concrete configuration, the ultrasound reception circuitry 120 is realized by, for example, a preamplifier, an A/D converter, a demodulator, a beam former, etc. The preamplifier performs gain correction by amplifying, for each channel, the reflected wave signals received by the ultrasound probe 101. The A/D converter converts the reflected wave signals after the gain correction into digital signals. The demodulator demodulates the digital signals. The beam former, for example, applies a delay time to the demodulated digital signals as required for determining the receive directivity, and adds up the digital signals applied with the delay time. The addition processing by the beam former generates reception signals in which a reflection component from the direction corresponding to the receive directivity is emphasized.

The internal memory 130 is constituted by, for example, a processor-readable storage medium such as a magnetic or optical storage medium, a semiconductor memory, etc. The internal memory 130 stores one or more programs for conducting ultrasound transmission/reception and for realizing functions of the processing circuitry 180, as well as various datasets, etc. In an exemplary implementation, such programs and datasets, etc. may be prestored in the internal memory 130. In another exemplary implementation, they may be first stored and distributed in the form of non-transitory storage media, and then read and installed from the media into the internal memory 130. The internal memory 130 is also adapted to store B-mode image data, contrast image data, blood flow-related image data, etc., generated by the processing circuitry 180, in response to operational inputs given via the input interface 150. The internal memory 130 may also be adapted to transfer the stored image data to the external device 104 or other entity via the communication interface 170.

Note that the internal memory 130 may at the same time be a drive unit, etc., adapted to read and write various information sets from and to portable storage media such as a CD drive, a DVD drive, and a flash memory. It is also possible for the internal memory 130 to write the stored data to portable storage media so that the data will be stored in the external device 104 via the portable storage media.

The image memory 140 is constituted by, for example, a processor-readable storage medium such as a magnetic or optical storage medium, a semiconductor memory, etc. The image memory 140 is adapted to store image data corresponding to multiple frames immediately preceding an input for a freeze operation given via the input interface 150. The image data stored in the image memory 140 is used in, for example, a continuous display (cine-display) operation.

It is not a requisite to realize the internal memory 130 and the image memory 140 by respective storage units independent of each other. The internal memory 130 and the image memory 140 may be realized by the same single storage unit. Also, the internal memory 130 and the image memory 140 may each be realized by multiple storage units.

The input interface 150 is adapted to accept a variety of instructions from an operator via the input device 102. The input device 102 may be, for example, a mouse, a keyboard, panel switches, slider switches, a trackball, a rotary encoder, an operation panel, and a touch command screen (TCS). The input interface 150 is connected to the processing circuitry 180 via, for example, a bus so that it converts operational instructions input by an operator into electric signals and outputs them to the processing circuitry 180. Note that the present embodiment does not limit the input interface 150 to a member for making connections to physical operational components such as a mouse and a keyboard. Examples of the input interface 150 also include a circuit that is adapted to receive electric signals corresponding to the operational instructions input from external input devices separate from the ultrasound diagnostic apparatus 1, and to output the electric signals to the processing circuitry 180.

The output interface 160 is an interface for outputting, for example, electric signals from the processing circuitry 180 to the output device 103. The output device 103 may be any discretionarily employed display such as a liquid crystal display, an organic EL display, an LED display, a plasma display, a CRT display, etc. The output device 103 may be a touch-panel type display serving also as the input device 102. The output device 103 may further include components such as a speaker for sound output, in addition to the display. The output interface 160 is connected to the processing circuitry 180 via, for example, a bus so that it outputs the electric signals from the processing circuitry 180 to the output device 103.

The communication interface 170 is connected to the external device 104 via, for example, the network NW so that it performs data communication with the external device 104.

The processing circuitry 180 is, for example, a processor functioning as a center of the ultrasound diagnostic apparatus 1. The processing circuitry 180 executes the programs stored in the internal memory 130 to realize functions corresponding to the programs. The functions performed by the processing circuitry 180 include, for example, a B-mode processing function 181, a Doppler processing function 182, an image generating function 183, a setting function 184 (setting process), a checking function 185 (diagnosing process), a report preparing function 186 (preparing process), a display controlling function 187 (display controlling process), and a system controlling function 188. While FIG. 1 assumes that the processing circuitry 180 as a single circuitry element realizes each of the various functions, the processing circuitry 180 may be constituted by a combination of multiple independent processors each running a program to realize the respective function. Note also that the B-mode processing function 181, the Doppler processing function 182, the image generating function 183, the setting function 184, the checking function 185, the report preparing function 186, the display controlling function 187, and the system controlling function 188 may be called a "B-mode processing circuit", a "Doppler processing circuit", an "image generating circuit", a "setting circuit", a "checking circuit", a "report preparing circuit", a "display controlling circuit", and a "system controlling circuit" and implemented as independent hardware circuits, respectively.

The B-mode processing function 181 is a function for generating B-mode data based on the reception signals from the ultrasound reception circuitry 120. In one example, the processing circuitry 180 with this B-mode processing function 181 performs envelope detection, logarithmic compression, etc., for the reception signals passed on from the ultrasound reception circuitry 120 to generate data (B-mode data) that expresses signal intensity by the degree of brightness. The generated B-mode data is stored in a RAW data memory (not illustrated) as B-mode raw data on two-dimensional ultrasound scan lines (rasters).

The Doppler processing function 182 is a function for generating data (Doppler information) as an extraction of Doppler effect-based motion information of a moving object that is present within the region of interest (ROI) set in a scan region, and this data is generated through the frequency analysis of the reception signals passed on from the ultrasound reception circuitry 120. The generated Doppler information is stored in the RAW data memory (not illustrated) as Doppler raw data (or Doppler data) on the two-dimensional ultrasound scan lines.

More specifically, the processing circuitry 180 with the Doppler processing function 182 estimates the motion information of the moving object including, for example, an average velocity, an average distribution, an average power, etc. at each of multiple sample points, and generates the Doppler data indicative of the estimated motion information. The moving object here is, for example, a blood flow, tissue portions such as the cardiac wall, a contrast medium, etc.

The image generating function 183 is a function for generating B-mode image data based on the data generated by the B-mode processing function 181. For example, the processing circuitry 180 with the image generating function 183 generates image data for display ("display image data") by a conversion process (scan conversion) of converting scan line signal sequences from the ultrasound scanning into scan line signal sequences in a video format as represented by televisions, etc. More specifically, the processing circuitry 180 subjects the B-mode raw data stored in the RAW data memory to raw-pixel conversion which, for example, is a coordinate conversion according to the scan configuration of the ultrasound probe 101, to generate pixel-based two-dimensional B-mode image data ("ultrasound image data"). In other words, the processing circuitry 180 with the image generating function 183 generates multiple ultrasound images (medical images) corresponding to the respective consecutive frames by utilizing the ultrasound transmission/reception.

Likewise, the processing circuitry 180 subjects the Doppler raw data stored in the RAW data memory to, for example, the raw-pixel conversion to generate Doppler image data providing blood flow information in the form of images. The Doppler image data may be average velocity image data, distribution image data, power image data, or image data including any combination thereof. The processing circuitry 180 generates, as the Doppler image data, more than one type of information including color Doppler image data showing colored blood flow information, gray-scale Doppler image data showing information of a single blood flow in wave-like gray scale, etc.

The setting function 184 is not performed in the first embodiment, so its description will be given later. For implementing the first embodiment, therefore, the setting function 184 may be omitted. The setting function 184 constitutes one example of a setting process.

The checking function 185 is a function for checking an ultrasound probe that includes multiple elements to transmit ultrasound signals and receive reflected wave signals from a given subject P or the air. Such a checking operation may be performed with an ultrasound diagnosis on a daily basis, and may also be performed during maintenance or routine checks of the apparatus. That is, the checking function 185 can be used not only by a physician, etc., who conducts ultrasound diagnoses, but also by a controller of the apparatus, a service engineer, etc., who has been assigned the maintenance work and the like. By way of example, the description of this embodiment will assume the user to be a physician such as a doctor. The term "check" or "checking" may be replaced by "test", "diagnosis", or the like. More specifically, the checking function 185 diagnoses the states of the elements based on one or more feature values of the reflected wave signals returned from the air. The feature value that can be suitably used here is, for example, an amplitude, a center frequency, or a bandwidth. In the case of an amplitude, for example, a sensitivity peak value may be used as the feature value. In more concrete terms, the maximum amplitude value (Vp-p) among the first reflected wave W1 is adopted as the sensitivity peak value. The states of the elements are data indicative of the differences between the initial data and the diagnosis data for the respective elements. The checking function 185 constitutes one example of a diagnosing process.

The report preparing function 186 is a function for preparing, based on the states that have been checked or diagnosed, deterioration degree information indicative of the degree of deterioration of the elements. For example, the report preparing function 186 may categorize the difference for each element, i.e., the data on its state obtained by the diagnosis, into one of multiple phases so as to prepare the deterioration degree information indicating, as the deterioration degree, the phase according to the size of the difference. As such, the larger the difference, the larger the deterioration degree. The expression "deterioration" here corresponds to the difference between the initial data and the diagnosis data for each element, and therefore, may also be called a "difference". Also, the "deterioration degree" may be called a "deterioration phase", a "deterioration type", a "deterioration rank", or the like.

Note that the report preparing function 186 may prepare the deterioration degree information in the form of a probe diagnosis report 200 as shown in FIG. 4, by preparing a first image 201 showing the positions of the elements and the deterioration degrees of the elements in association with each other, and including this first image 201 in the deterioration degree information together with the identification information of the ultrasound probe 101. The report preparing function 186 stores the prepared probe diagnosis report 200 in the internal memory 130. Note that the report preparing function 186 may cause a printer, as a part of the output device 103, to print out the prepared probe diagnosis report 200. Also, the report preparing function 186 may store the prepared probe diagnosis report 200 in one or more external storage media. The deterioration degree information prepared by the report preparing function 186 may further associate the positions of the elements with symbols according to the deterioration degrees of the respective elements. Instead of such symbols varying according to the deterioration degrees, colors varying according to the deterioration degrees may be used. Or, colors varying according to the deterioration degrees may be used in addition to the symbols varying according to the deterioration degrees. Hereinafter, the "identification information of the ultrasound probe 101" may also be called "probe identification information". FIG. 4 illustrates an instance where the probe diagnosis report 200 is superimposed on an ultrasound image and displayed together by a display 103a as a part of the output device 103.

The probe diagnosis report 200 here may take any form as long as it serves as the deterioration degree information containing the first image 201 and the identification information of the ultrasound probe 101, and may discretionarily contain any other information. The example shown in FIG. 4 contains probe-related information (including the probe identification information), the first image 201, and a message, as probe diagnosis report 200.

The probe-related information includes, for example, an operator name, a model name, a probe type, a system serial number, and a probe serial number (the probe identification information). The operator name is the name of an operator who has started up the ultrasound diagnostic apparatus 1. As the operator name, for example, a user name input at the login action for starting up the ultrasound diagnostic apparatus 1 may be used. The model name is one example of instrument information for identifying the instrument model corresponding to the ultrasound probe 101. The probe type is information indicative of the types or design of probes, such as a linear array type, a phased array type, and so on. The system serial number is a production number of the apparatus for checking the ultrasound probe 101, and such an apparatus may be the ultrasound diagnostic apparatus 1 or a probe diagnosing apparatus (not illustrated). The probe serial number is a probe production number identifying the ultrasound probe 101 as an individual member. The probe serial number is one example of probe identification information for identifying the individual ultrasound probe 101.

The first image 201 shows the positions of the elements and the deterioration degrees of the elements in association with each other. For example, the first image 201 is prepared in such a manner that the multiple elements are grouped into a number of groups fewer than the number of the elements based on the positions of the respective elements, and the applicable deterioration degree is associated with each of the groups. In one concrete exemplary configuration, where 128 elements are arranged from the right to the left, the deterioration degrees of 16 elements may be indicated in one block, so that the deterioration degrees of the 128 elements are indicated in 8 blocks. More specifically, the 128 elements are allocated to 8 element groups for every 16 elements. Then, the deterioration degrees of the respective 8 element groups are indicated in 8 blocks so that the deterioration degrees of the 128 elements are represented by the deterioration degrees of the 8 element groups. Note that the number of elements, the number of blocks, and the number of element groups here are only examples, and the embodiment is not limited to such numbers. The description may simply say "group" to refer to the element group. Turning to the first image 201 shown in FIG. 4, the first to eighth element groups give their respective deterioration degrees sequentially from the right. To the first element group, the 1st to 16th elements from the right are allocated. The 17th to 32nd elements are allocated to the second element group. The 33rd to 48th elements are allocated to the third element group. The 49th to 64th elements are allocated to the fourth element group. The 65th to 80th elements are allocated to the fifth element group. The 81st to 96th elements are allocated to the sixth element group. The 97th to 112th elements are allocated to the seventh element group. The 113th to 128th elements are allocated to the eighth element group.

The deterioration degree of elements that may be adopted here for representing each element group is the largest deterioration degree among the deterioration degrees of the 16 elements included in the element group. In the disclosure herein, six phases are used to show the deterioration degrees and they consist of "Healthy" and types A to E from the smallest deterioration. "Healthy" is a phase in which the element involves substantially no deterioration, or a deterioration (difference) within the range of the specifications. Type E is a phase in which the element involves a significant deterioration, or the element is considered to be a defect. Types A to D are phases between the healthy phase and the type E phase, and they are indicative of respective deterioration degrees which sequentially increase from the type A phase toward the type D phase (A<B<C<D). Note that the indications of the deterioration degrees are not limited to six phases, and any number of phases may be discretionarily adopted. In the example shown in FIG. 4, the deterioration degrees of the elements in the first, the second, and the third element groups from the right are all "Healthy". The deterioration degree of the elements in the fourth element group is "Out of spec Type A". Here, the deterioration degree "Out of Spec Type. A" of the elements in the fourth element group is based on the individual deterioration degrees of the 49th to 64th elements, which are respectively "Healthy", "Healthy", "Out of Spec Type A", where "Healthy", and the largest deterioration degree among them (i.e., "Out of Spec Type A") is adopted. The deterioration degree of the fifth element group is "Out of spec Type B". That is, the deterioration degree "Out of Spec Type B" of the fifth element group is based on the individual deterioration degrees of the 65th to 80th elements, which are respectively "Healthy", "Out of Spec Type A", "Out of Spec Type B", and "Healthy", where the largest deterioration degree among them (i.e., "Out of Spec Type B") is adopted. The deterioration degrees of the sixth and seventh element groups are both "Out of spec Type A". The deterioration degree of the eighth element group is "Healthy". Note also that FIG. 4 shows an example where the display uses different colors for different deterioration degrees. Nevertheless, the deterioration degrees may be presented as a text string, a symbol, etc., such as "Healthy" or "Type A", and the same color may be used for the display of multiple indications of the deterioration degrees. When a multi-color display for different deterioration degrees is adopted, the symbols, etc. for indicating the deterioration degrees may be omitted.

The message in the probe diagnosis report 200 is a text string provided for a physician according to the deterioration degree, and given through a message area in the probe diagnosis report 200. Examples that may be suitably used as the message include comments for assisting the physician's comprehension or prompting the operators action, such as notes about the deterioration degree of elements, an influence on the image diagnosis operations, a need for maintenance, and so on. The message may be replaced by "comments", "comments and messages", or the like. For providing such a message, for example, text strings corresponding to comments and messages may be prestored in the internal memory 130 in association with the deterioration degrees as shown in FIG. 5, so that the applicable stored text strings can be set forth. In one example, the report preparing function 186 may search the internal memory 130 based on the largest "deterioration degree" among the deterioration degrees of the elements in all the element groups, and set forth the text string included in the retrieved "comments and messages" through the message area in the probe diagnosis report 200.

Figure 6:
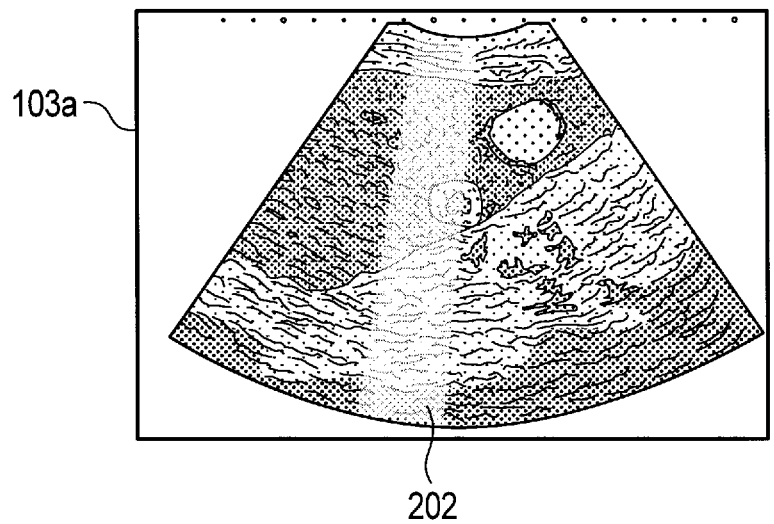
FIG. 6 is a schematic diagram showing an image according to the first embodiment, which is superimposed on an ultrasound image for display so that a region involving a large degree of deterioration is covered.

The report preparing function 186 may also prepare the deterioration degree information in the form of, for example, a second image 202 as shown in FIG. 6, which is an image including one or more straight lines to cover, among the multiple regions in an ultrasound image created based on outputs of multiple elements, the region based on outputs of the elements involving a larger degree of deterioration than a threshold. As one example, when the 49th to 80th elements from the right involve a larger degree of deterioration than the threshold, the second image 202 is a linear image covering the region that is based on the outputs of these 49th to 80th elements. Note that, while the second image 202 shown in FIG. 6 is intended to be an image including 32 straight lines that cover the region based on the outputs of 32 elements, its appearance on the figure is an image constituted by one thick line. Also, the second image 202 here is a semitransparent image that allows the underlying ultrasound image to be seen in pale colors. Such a semitransparent image may have any transparency from 0% (opaque) to 100% (fully transparent), but preferably has an intermediate transparency of, for example, about 50%±20%. The transparency of the second image 202 may be changed according to the deterioration degrees, or may be left unchanged. Also, other than the transparency, any property such as transmittance, opacity, or the like may be discretionarily used for the see-through characteristics of the images to be used. Further, the second image 202 may have a color or colors the same as or different from a color or colors indicating the respective, corresponding deterioration degrees. FIG. 6 illustrates an instance where the second image 202 is superimposed on the ultrasound image and displayed together by the display 103*a*. The report preparing function 186 constitutes one example of a preparing process.

The display controlling function 187 is a function for controlling the display as the output device 103 to display images based on various types of ultrasound image data generated by the image generating function 183. More specifically, and for example, the processing circuitry 180 with the display controlling function 187 controls display presentation of images which are based on the image data such as the B-mode image data and the Doppler image data generated by the image generating function 183 or the combination thereof. The display controlling function 187 also superimposes the deterioration degree information prepared by the report preparing function 186 onto the ultrasound image of the subject P so that the resultant image is presented through the display. For performing a preview display before ultrasound inspection of the subject P, the display controlling function 187 may control the display to display only the deterioration degree information, as no ultrasound image of the subject P is available yet. In an exemplary configuration, the processing circuitry 180 with the display controlling function 187 also accepts a command for selecting various display modes, etc. via the input interface 150. Such various display modes include, for example, a display mode for displaying an ultrasound image, a first display mode for displaying an ultrasound image on which the probe diagnosis report as discussed above is superimposed, a second display mode for displaying an ultrasound image on which the second image as discussed above is superimposed, and so on.

As a concrete configuration, the processing circuitry 180 with the display controlling function 187 performs, for example, conversion (scan conversion) of scan line signal sequences from the ultrasound scanning into scan line signal sequences in a video format as represented by televisions or the like, to generate display image data. The processing circuitry 180 may further subject this display image data to various types of processing such as processing for the corrections of dynamic range, brightness (luminance), contrast, and a y-curve, as well as processing for RGB conversion. The processing circuitry 180 may also put to the display image data additional information such as text information, scale marks, body marks, etc., based on various parameters. The processing circuitry 180 may optionally generate a user interface (graphical user interface: GUI) for prompting the operator to input various instructions via the input device, and cause the display to display the GUI.

The system controlling function 188 is a function that takes total control over the operations of the ultrasound diagnostic apparatus 1. For example, the processing circuitry 180 with the system controlling function 188 controls the ultrasound transmit circuitry 110 and the ultrasound reception circuitry 120 based on parameters for the ultrasound transmission and reception. In an exemplary configuration, the processing circuitry 180 with the system controlling function 188 also accepts a command for selecting various imaging modes via the input interface 150. The various imaging modes include, for example, a B-mode, a Doppler mode, an elastography mode, and so on.

Next, operations of the ultrasound diagnostic apparatus 1 configured as above will be described with reference to the flowcharts in FIGS. 7, 8, 10, and 11, and the schematic diagram in FIG. 9. The operations of the ultrasound diagnostic apparatus 1 include an ultrasound probe diagnosing method performed by the ultrasound diagnostic apparatus 1. The description will assume that the apparatus main body 100 of the ultrasound diagnostic apparatus 1 is connected to one or more ultrasound probes 101 having surfaces of their probe elements cleaned in advance. It will also be assumed that, for any ultrasound probes to be connected freshly, their probe connectors as well as surfaces of their probe elements are already cleaned. Each of such ultrasound probes 101 includes multiple elements for transmitting ultrasound signals and receiving reflected wave signals from the subject P or the air.

Figure 7:
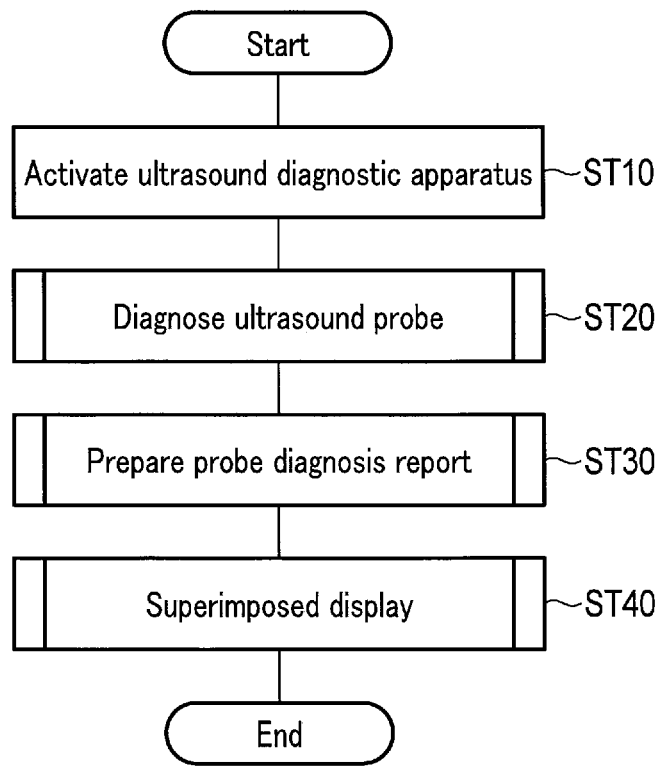
FIG. 7 is a flowchart for explaining an outline of operations according to the first embodiment.

First, step ST10 as shown in FIG. 7 is performed, where the ultrasound diagnostic apparatus 1 is activated in response to an operation by a physician such as a doctor.

After step ST10, step ST20 is performed, where the processing circuitry 180 of the ultrasound diagnostic apparatus 1 diagnoses the ultrasound probe 101 adapted to transmit ultrasound signals and receive reflected wave signals from the air. More specifically, the processing circuitry 180 diagnoses the states of the elements based on one or more feature values of the reflected wave signals returned from the air. This step ST20 proceeds with, for example, steps ST21 to ST25 as shown in FIG. 8.

Here, in step ST21, the processing circuitry 180 first detects an operation by the physician on a start button.

In step ST22, upon detection of the operation on the start button, the processing circuitry 180 diagnoses the ultrasound probe 101. More specifically, the processing circuitry 180 causes ultrasound signals to be transmitted in the air and have the multiple elements of the ultrasound probe 101 receive the reflected wave signals from the air, so that the states of the elements are diagnosed based on one or more feature values of the reflected wave signals.

In step ST23, the processing circuitry 180 determines whether or not a loose connection is suspected based on the diagnosis result, and if it is determined that a loose connection is suspected, the operation flow proceeds to step ST24. If not, the operation flow proceeds to step ST25.

In step ST24, the processing circuitry 180 causes the display 103a to display a retry message Rm1 and a start button Bt1 as shown in FIG. 9. Thereafter, the operation flow returns to step ST21. During the interval for returning from step ST24 to step ST21, the ultrasound diagnostic apparatus 1 has the connection between the ultrasound probe 101 and the apparatus main body 100 checked through the action of attachment or detachment of the ultrasound probe 101 by the physician, cleaning of the probe connector, or the like.

In step ST25, the processing circuitry 180 determines whether or not the diagnosis of the states of the elements has been completed. In one example, the determination performed by the processing circuitry 180 in step ST25 includes determining whether or not all the one or more ultrasound probes 101 connected to the apparatus main body 100 have been diagnosed for their element states. If the determination result in step ST25 is "No", the operation flow returns to step ST22 so that the diagnosis of the one or more ultrasound probes 101 is continued. If the determination result in step ST25 indicates completion of the diagnosis, the operations in step ST20 are ended. Therefore, step ST20 constituted by steps ST21 to ST25 is finished.

After step ST20, step ST30 is performed, where the processing circuitry 180 of the ultrasound diagnostic apparatus 1 prepares, based on the diagnosed states, the deterioration degree information indicative of the degree of deterioration of the elements. This step ST30 proceeds with, for example, steps ST31 to ST35 as shown in FIG. 10.

In step ST31, the processing circuitry 180 reads, in response to an operation of selecting the ultrasound probe 101 by the physician, the result of diagnosing the states of the elements in the selected ultrasound probe 101 from the internal memory 130.

In step ST32 after step ST31, the processing circuitry 180 detects an operation by the physician on a report preparation button. Note that such operations by the physician in steps ST31 to ST32 may be omitted based on a setting. That is, the operations in steps ST20 to ST30 may be sequentially performed as a series of operations in accordance with the setting for omitting the physician's operations.

In step ST33 after step ST32, the processing circuitry 180 prepares the first image 201 by associating the positions of the elements and the deterioration degrees of these elements based on the diagnosis result acquired by the reading operation in step ST31. The processing circuitry 180 then prepares the probe diagnosis report 200 containing the first image 201 and the identification information of the corresponding ultrasound probe 101.

In step ST34 after step ST33, the processing circuitry 180 subjects this probe diagnosis report 200 to a preview display operation. The physician is thereby enabled to confirm the probe diagnosis report 200 for the ultrasound probe 101 selected in relation to step ST31. The confirmed probe diagnosis report 200 is stored in the internal memory 130.

In step ST35 after step ST34, the processing circuitry 180 determines whether or not the operations for all the one or more ultrasound probes 101 that the physician wants to confirm have been completed. Here, all the one or more ultrasound probes 101 desired by the physician for confirmation refer to at least one ultrasound probe 101 among all the ultrasound probes 101 for which checking or diagnosing has been conducted. Accordingly, in one example, the processing circuitry 180 performs the determination in step ST35 according to whether or not an operation on an applicable end button has been detected. If the determination in step ST35 is "No", the operation flow returns to step ST31 so that the above-described operations in steps ST31 to ST35 will be repeated. If the determination result in step ST35 indicates completion of the desired operations, the operations in step ST30 are ended. Therefore, step ST30 constituted by steps ST31 to ST35 is finished.

Figure 11:
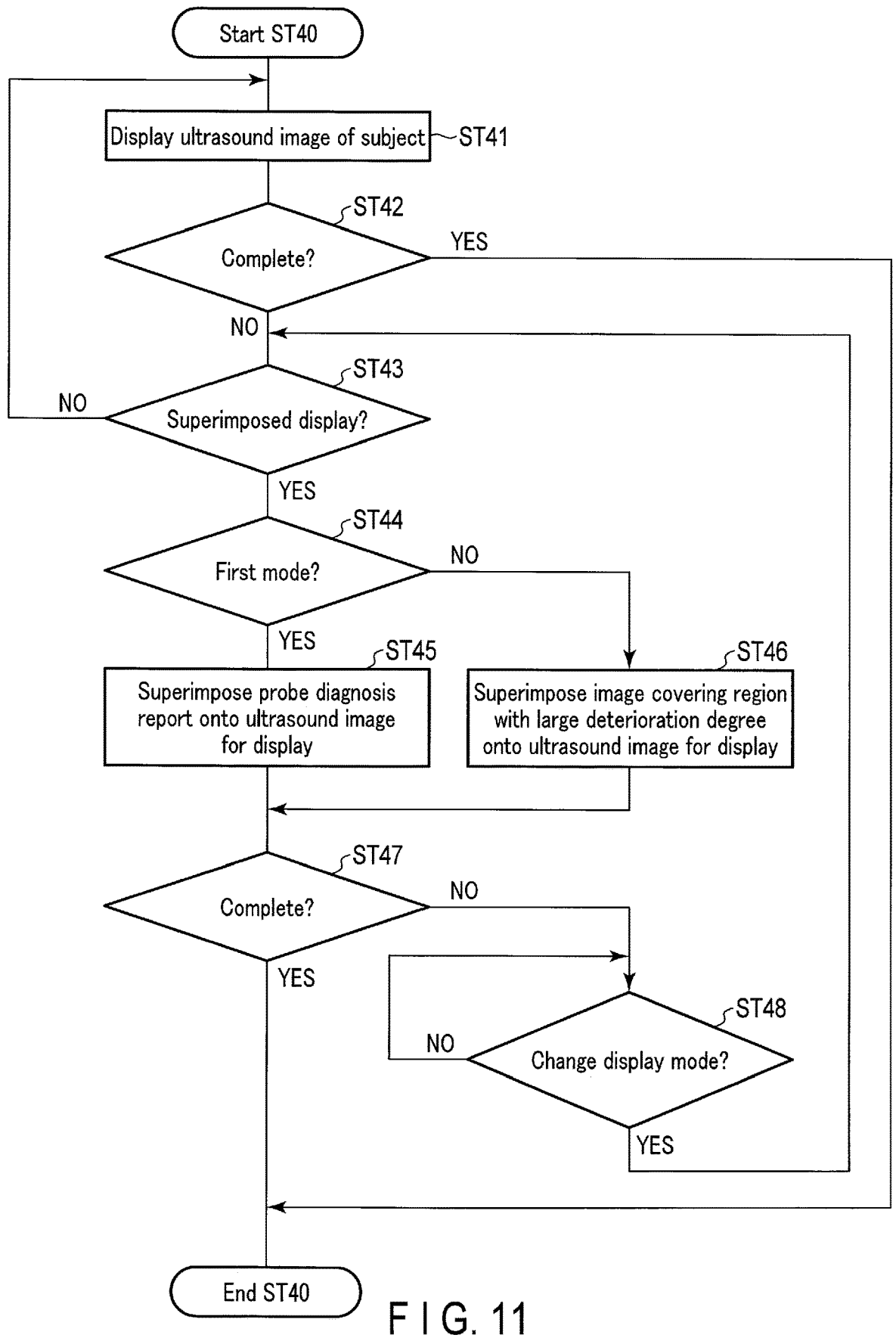
FIG. 11 is a flowchart for explaining operations in step ST40 according to the first embodiment.

After step ST30, step ST40 is performed, where the processing circuitry 180 of the ultrasound diagnostic apparatus 1 superimposes the probe diagnosis report 200 (the deterioration degree information) prepared in step ST30 onto the ultrasound image of the subject P, and causes the display 103a to display the resultant image. This step ST40 proceeds with, for example, steps ST41 to ST48 as shown in FIG. 11.

In step ST41, first, the ultrasound diagnostic apparatus 1 scans the inside of the subject P using ultrasound signals, with the ultrasound probe 101 placed in contact with the subject P by the physician's operation, and generates an ultrasound image based on the output from the ultrasound probe 101 that has received reflected wave signals. The ultrasound diagnostic apparatus 1 accordingly displays an ultrasound image of the subject P through the display 103a. The physician conducts ultrasound diagnosis while looking at the ultrasound image on display.

In step ST42 after step ST41, the processing circuitry 180 determines whether or not the ultrasound diagnosis of the subject P has been completed. In one example, the processing circuitry 180 performs the determination in step ST42 according to whether or not an operation on an applicable end button has been detected. If the determination result in step ST42 indicates completion of the diagnosis of the subject P, the operations in step ST40 are ended. If the determination result in step ST42 is "No", the operation flow proceeds to step ST43.

In step ST43 after step ST42, the processing circuitry 180 determines whether or not the probe diagnosis report 200 (the deterioration degree information) will be subjected to the superimposed display on the ultrasound image of the subject P. In one example, the processing circuitry 180 performs the determination in step ST43 according to whether or not an operation on a mode transition button for the transition to the first display mode or the second display mode has been detected. If the determination result in step ST43 is "No", the operation flow returns to step ST41 so that the display of the ultrasound image of the subject P is continued. On the other hand, if the determination result in step ST43 indicates that the superimposed display is to be performed, the operation flow proceeds to step ST44.

In step ST44, the processing circuitry 180 determines whether or not the designation by the mode transition button is the first display mode. If this determination result indicates the first display mode, the processing circuitry 180 advances to the operation in step ST45. Also, if the determination result in step ST44 is "No" (that is, if the result indicates the second display mode), the processing circuitry 180 advances to the operation in step ST46.

In step ST45, the processing circuitry 180 superimposes the probe diagnosis report 200 onto the ultrasound image of the subject P and displays the resultant image.

In step ST46, the processing circuitry 180 superimposes the second image 202 for covering the region with a large deterioration degree, onto the ultrasound image of the subject P and displays the resultant image.

In step ST47 after step ST45 or ST46, the processing circuitry 180 determines whether or not the superimposed display of the deterioration degree information of the ultrasound probe 101 will be ended. In one example, the processing circuitry 180 performs the determination in step ST47 according to whether or not an operation on an applicable end button has been detected. If the determination result in step ST47 is "No", the operation flow proceeds to step ST48.

In step ST48, the processing circuitry 180 determines whether or not the display mode should be changed, and if the determination result is "No", the determination in step ST48 is repeated. According to steps ST47 to ST48, the determination in step ST48 is repeated in the absence of the physician's operation on the button, so that the superimposed display under the current display mode continues.

If the determination result in step ST48 indicates that the display mode should be changed, the operation flow returns to step ST43. For example, for a switchover of the display mode from the first display mode of performing the superimposed display of the probe diagnosis report 200 to the second display mode of performing the superimposed display of the second image 202, the operation flow returns to step ST43, proceeds to step ST44 where the determination is "No" (that is, the second display mode is indicated), and proceeds to step ST46 with this determination result. Similarly, if, as another example, a switchover of the display mode is from the second display mode to the first display mode, the operation flow returns to step ST43, proceeds to step ST44 where the determination is indicative of the first display mode, and proceeds to step ST45. As yet another example, if the second display mode of performing the superimposed display of the second image 202 is to be switched to the display mode without the superimposed display of the deterioration degree information, the operation flow returns to step ST43, and then further returns to step ST41 from step ST43.

If the determination result in step ST47 indicates the end of the superimposed display, the operations in step ST40 are ended. Therefore, step ST40 constituted by steps ST41 to ST48 is finished.

In conjunction with the end of step ST40, the ultrasound diagnostic apparatus 1 terminates the ultrasound inspection of the current subject P. The ultrasound diagnostic apparatus 1 performs step ST40 in a similar manner for another subject P.

As described above, the first embodiment employs an ultrasound diagnostic apparatus that can be connected with an ultrasound probe including multiple elements adapted to transmit ultrasound signals and to receive reflected wave signals from a subject or from the air, and that is capable of generating ultrasound images based on outputs from the multiple elements. The ultrasound diagnostic apparatus here diagnoses the states of the elements based on one or more feature values of the reflected wave signals returned from the air. The ultrasound diagnostic apparatus also prepares, based on the states that have been diagnosed, deterioration degree information indicative of the deterioration degrees of the elements. Moreover, the ultrasound diagnostic apparatus superimposes the deterioration degree information onto an ultrasound image of the subject and causes a display to display the resultant image.

This configuration allows the physician, etc. to comprehend the deterioration, defects, and so on of the elements in the ultrasound probe during the ongoing ultrasound inspection of the subject.

Additionally, it is often the case that the elements in the ultrasound probe in a general ultrasound diagnostic apparatus deteriorate, malfunction, etc. in accordance with how the ultrasound probe has been used or due to dropping or the like of the ultrasound probe, even if the ultrasound probe is periodically or non-periodically subjected to diagnosis work. This could result in a situation where the physician conducts the ultrasound inspection of a subject while she or he is unaware of the deterioration or malfunction of the elements. Then, ultrasound images that cannot provide a sufficient sensitivity required for image diagnosis due to the deterioration, or ultrasound images that have not been properly constructed due to the defective elements, might be used in the image diagnosis. Furthermore, it is difficult for the physician to know which part of ultrasound images the deterioration of the elements would affect during the ultrasound inspection of a subject. It is also impractical for the physician to practice daily ultrasound inspection operations with the ultrasound diagnostic apparatus while constantly paying attention to the deterioration, etc. of the ultrasound probe.

In view of the foregoing, it is necessary to provide the results of checking the ultrasound probes to the physician in an easy-to-understand manner for the sake of reliable inspections and also for the sake of ultrasound inspection operations supported by the knowledge about deterioration in the probes. According to the first embodiment, the probe conditions can be displayed in association with ultrasound images so that the physician can grasp deterioration degrees of the elements in ultrasound probes. Also, the embodiment enables the physician to recognize the presence or absence of defective elements that involve a large deterioration degree. Moreover, as the physician can comprehend the deterioration, defects, etc. of the elements, the embodiment allows for the following effects (i) to (iii).

(i) Inspection events with a deteriorated ultrasound probe will be reduced, and accordingly, more accurate image diagnosis will be enabled and the occurrence of overlooking a lesion will be suppressed. That is, since the probe conditions are displayed in association with ultrasound images, the physician can conduct inspections while being readily informed of the device state, and this can contribute to reliable inspections and appropriate diagnoses.

(ii) Since inspection events with a deteriorated ultrasound probe will be reduced, repetition of inspections will be prevented, and the time and number of the inspections will be reduced. Consequently, the burden on the physician and the subject (patient) can be mitigated.

(iii) Conditions of ultrasound probes can be tracked, and therefore, the time for the replacement of probes can be accurately specified by the physician.

According to the first embodiment, the deterioration degree information may be prepared in the form of a probe diagnosis report containing the first image and the identification information of an ultrasound probe, in which the first image is prepared to show the positions of the elements in the ultrasound probe and the deterioration degrees of the elements in association with each other. In this configuration, the probe diagnosis report is superimposed on an ultrasound image of the subject for display, and accordingly, the physician can comprehend the position of the elements and the deterioration degrees of the elements about the ultrasound probe identified by the identification information.

According to the first embodiment, the deterioration degree information may also be prepared in the form of the second image including one or more straight lines to cover, among the multiple regions in an ultrasound image created based on outputs of multiple elements, the region based on outputs of the elements involving a larger degree of deterioration than a threshold. In this configuration, the second image is superimposed on an ultrasound image of the subject for display, and accordingly, the physician can comprehend the region involving a larger degree of deterioration among the ultrasound image.

According to the first embodiment, moreover, the deterioration degree information may be prepared by further associating the positions of the elements with symbols according to the deterioration degrees of the elements. In this configuration, the respective deterioration degrees can be comprehended by the physician reading the symbols.

Second Embodiment

The second embodiment relates to a form of displaying the result of a probe check with a display pattern changed according to the scan conditions, the number of image forming elements, etc. In one example, if a change in the depth as one of the scan conditions updates the part corresponding to a deteriorated element or a defective element, the display pattern is changed according to the second image reflecting the updated part, and the probe check result is superimposed on an ultrasound image with the changed display pattern and displayed.

More specifically, in addition to the functions or operations described above, the processing circuitry 180 with the display controlling function 187 corrects the deterioration degree information based on the scan conditions for the ultrasound image of the subject P and also on the number of elements that form the image of a display target among the ultrasound image of the subject P. The processing circuitry 180 with the display controlling function 187 then superimposes the corrected deterioration degree information onto the image of the display target, and causes the display 103a to display the resultant image.

Here, the scan conditions include, for example, the coverage of a scan cross-section (the depth for ultrasound transmission/reception and the range of angles), the number of scan lines included in each scan cross-section, the density of scan lines, the scan line for starting ultrasound transmission/reception in the respective scan cross-section (the starting scan line), the order of ultrasound transmission/reception for the scan lines in each scan cross-section (the sequence of transmission/reception), and so on.

The number of elements that form the image of a display target may be, for example, the number of elements that receive the reflected wave signals for constructing an ultrasound image to be actually displayed, among the 128 elements arranged in the head of the ultrasound probe 101. The expression, "the number of elements that form the image of a display target" may be replaced by, for example, "the size of the image of a display target" or "the size of the displayed image".

The remaining aspects are the same as the first embodiment.

Based on the above configuration, it will be supposed that, as the previously described operation in step ST46, the second image 202 is now superimposed on an ultrasound image of the subject P and displayed on the display 103a as shown in the upper illustration in FIG. 12. In this example, the ultrasound image is an image based on the outputs of the 128 elements, and the second image 202 is an image corresponding to the region based on the outputs of the 49th to 80th elements among the 128 elements occupying the right-to-left space. Subsequently, the ultrasound diagnostic apparatus 1 subjects a display target Tg (indicated by broken lines in the figure) to an enlarged display in response to a zoom operation by the physician. The zoom operation here is supposed to be, for example, an operation for decreasing the scan condition "depth" and displaying an ultrasound image based on the outputs of the 17th to 112th elements, i.e., a ¾ proportion, of the 128 elements arranged from the right to the left.

The processing circuitry 180 of the ultrasound diagnostic apparatus 1 corrects the second image 202 based on the scan conditions and the number of elements that form the image of the display target Tg, as updated by the zoom operation. For example, based on the scan depth becoming shallower, and the number of elements that form the ultrasound image becoming ¾, the processing circuitry 180 decreases the depth of the second image 202 and halves the number of elements forming the second image 202. Note that, here, the number of elements forming the second image 202 is halved in such a manner that the element involving the largest deterioration degree is included. The second image 202 is therefore corrected to correspond to, for example, the region based on the outputs of the 65th to 80th elements as a left half of the 49th to 80th elements. The proportions mentioned here, such as "¾" and "half" (½), are non-limiting examples and may be discretionarily changed. As a supplementary note, there is a demand for specifying a region under the influence of a defective element by use of a narrow range when enlarged ultrasound images are subjected to observation. It is preferable from the viewpoint of this demand that the ratio rA of the number of elements forming the second image 202 after the correction to the number before the correction be smaller than the ratio rB of the number of elements forming the ultrasound image after the updating to the number before the updating. Such a relationship rA c rB is valid in the above example where rA=½ and rB=¾. However, establishing the relationship rA<rB is not essential. Instead, a different relationship such as rA rB may be adopted.

After correcting the second image 202, the processing circuitry 180 superimposes the corrected second image 202 onto the image of the display target and causes the display 103a to display the resultant image as shown in the lower illustration in FIG. 12. Notice that the second image 202 after the correction has a range narrower than the second image 202 before the correction, even though the ultrasound image has been enlarged. Therefore, the second image 202 after the correction can show the region involving a large deterioration degree in more detail, along with the zoom operation of the ultrasound image of the subject P. This configuration accordingly contributes to a highly successful image diagnosis.

According to the second embodiment as described above, the deterioration degree information is corrected based on scan conditions for an ultrasound image of the subject P and also on the number of elements that form the image of a display target among the ultrasound image of the subject P, and the corrected deterioration degree information is superimposed on the image of the display target so that the resultant image is presented through the display. Accordingly, in addition to providing the effects of the first embodiment, the second embodiment realizes an effect of enabling the superimposed display with the deterioration degree information corrected according to changes in scan conditions and display target images.

Third Embodiment

Figure 13:
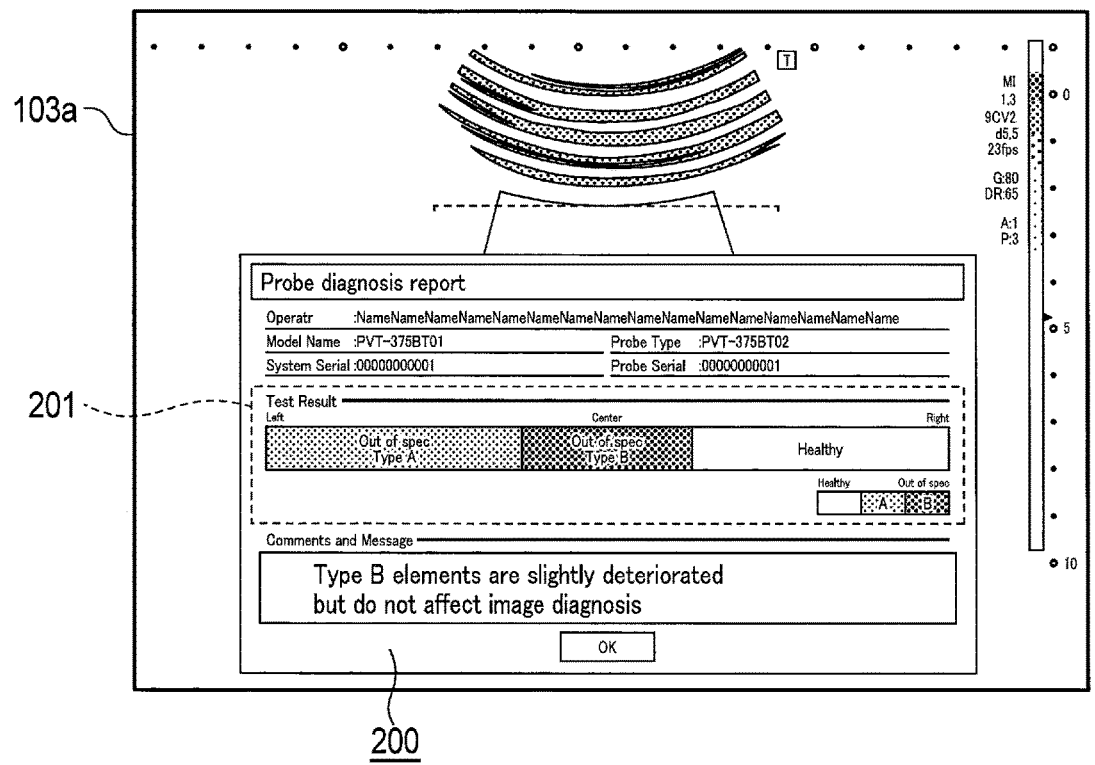
FIG. 13 is a schematic diagram for explaining a probe diagnosis report according to a third embodiment.

The third embodiment relates to a concrete form of the group display in which the deterioration degrees of the elements in the ultrasound probe 101 are handled together and displayed for the respective groups. The description of the first embodiment has assumed that the elements are grouped into eight groups and the deterioration degrees are displayed for the respective eight groups. In the third embodiment, the display operation is conducted with a reduced number of element groups. For example, as shown in FIG. 13, the elements may be grouped into three groups, namely, the center, left, and right groups, so that the deterioration degrees of the elements are displayed for the respective three groups. In another instance, the elements may be split into two groups on the left and right sides, so that the deterioration degrees are displayed for the respective two groups. The smallest unit of groups for display is each individual element. That is, the numbers of element groups discussed here are only examples and do not pose a limitation. According to the third embodiment, as such, the deterioration degrees of the elements may also be displayed as the first images 201 or the second images 202 for the corresponding respective groups.

In this relation, the processing circuitry 180 with the report preparing function 186 prepares the deterioration degree information as described above, i.e., in such a manner that the multiple elements are grouped into a number of groups fewer than the number of the elements based on the positions of the respective elements, and the applicable deterioration degree is associated with each of the groups. Also, the report preparing function 186 may split the elements into groups and display the deterioration degrees of the elements for the respective element groups in accordance with the group number input by the physician's operation. As another exemplary configuration, the report preparing function 186 may cause the display 103a to display group numbers "8", "2", "3", and "128", and split the elements into groups in accordance with the group number selected by the physician's operation so that the deterioration degrees of the elements are displayed for the respective element groups.

FIG. 13 illustrates, as one exemplary form, the first image 201 that shows three groups, i.e., the right group, the center group, and the left group, constituted by the 128 elements split into these groups according to the selected group number "3". The right group corresponds to the combination of the 1st to 3rd element groups from the right, shown in FIG. 4. The center group corresponds to the combination of the 4th and 5th element groups from the right, shown in FIG. 4. The left group corresponds to the combination of the 6th to 8th element groups from the right, shown in FIG. 4. As the deterioration degree indicated by each of the right, center, and left groups here, the largest deterioration degree among the deterioration degrees of the element groups included in the respective groups may be used.

The second image 202 is prepared using the combinations of the element groups as in the case of the first image 201. For example, as the second image 202 that corresponds to the first image 201 shown in FIG. 13, a region having about a ⅖ width of an ultrasound image may be displayed as in the upper illustration in FIG. 12.

The remaining aspects are the same as the first or the second embodiment.

With the above configuration, it is possible to perform the operation in said step ST45 in such a manner as to group the elements in the ultrasound probe 101 into, for example, three groups including the center, right, and left groups as shown in FIG. 13 so that the deterioration degrees are handled together and displayed on the display 103a for the respective three groups.

According to the third embodiment as described above, the deterioration degree information is prepared by grouping the multiple elements into a number of groups fewer than the number of the elements based on the positions of the respective elements, and associating the applicable deterioration degree with each of the groups. Therefore, the same effects as in the first or the second embodiment can be attained.

Fourth Embodiment

The fourth embodiment relates to a form of expressing the sensitivity deterioration degrees for the respective element groups by symbols (e.g., "Healthy"<A<B<C<D<E) and colors (e.g., white<pale<intermediate<dark) as shown in FIG. 14(a) to (c).

For example, a deterioration degree of substantially zero is expressed by the symbol "Healthy" and white. Also for example, a small deterioration degree is expressed by the symbol "A" or "B" and a pale color. A large deterioration degree may be expressed by the symbol "C" or "D" and an intermediate color. A significantly large deterioration degree, similar to that of a defect, may be expressed by the symbol "E" and a dark color. Note that these symbols for six phases and color types for four phases are only examples and do not pose a limitation. The pale color that can be employed here may be any non-prominent color and its examples include light yellow, cream, ivory, and beige. The dark color may be any color, such as red for example, that can call attention to itself. The intermediate color may be brown, ocher, etc., or any color categorized between the pale and dark colors. The embodiment, however, is not limited to such a hue-varying configuration, and may instead be of a configuration that uses a color of the same hue and creates a pale color by increasing a white portion and a dark color by increasing a black portion.

The processing circuitry 180 with the report preparing function 186 prepares the deterioration degree information by individually associating the positions of the elements with the colors according to the deterioration degrees of the respective elements. As the colors according to the deterioration degrees, for example, a darker color may be used for a larger deterioration degree. The report preparing function 186, in preparing the deterioration degree information, further associates the positions of the elements with the symbols according to the deterioration degrees of the respective elements. However, when the deterioration degrees are expressed by colors, the symbols for expressing the deterioration degrees may be omitted.

The remaining aspects are the same as any of the first to third embodiments.

Figure 14:
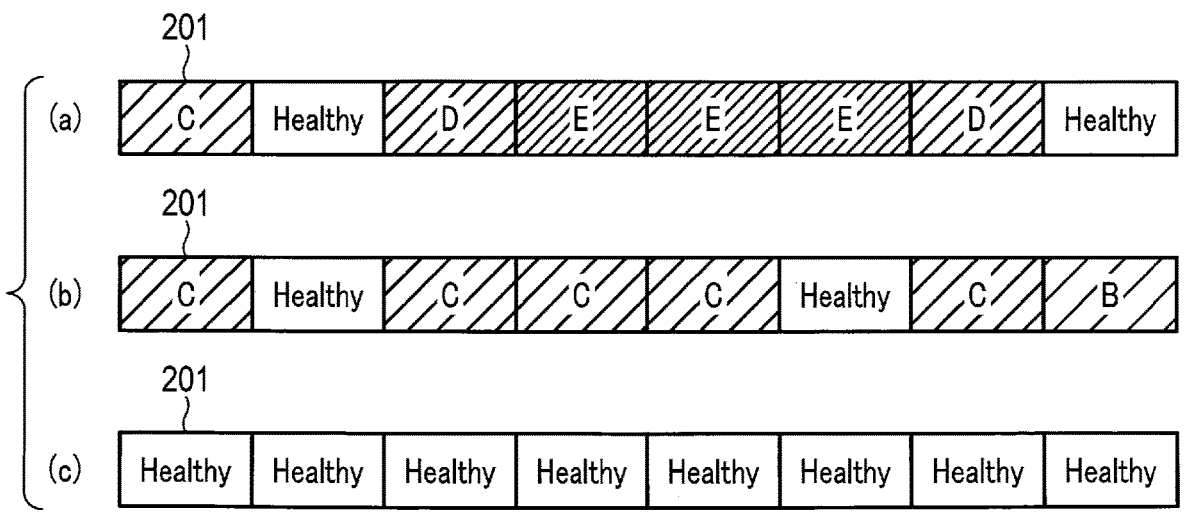
FIG. 14 is a schematic diagram showing examples of a first image appearing in a probe diagnosis report according to a fourth embodiment.

Based on the above configuration, it is possible to perform the operation in said step ST45 in such a manner as to superimpose the probe diagnosis report 200 containing the first image 201 as shown in, for example, any of FIG. 14(*a*) to (*c*), onto an ultrasound image of the subject P, so that the display 103*a* displays the resultant image.

According to the fourth embodiment as described above, the deterioration degree information is prepared by individually associating the positions of the elements with the colors according to the deterioration degrees of the respective elements. Accordingly, while providing effects similar to the first to third embodiments, the fourth embodiment further realizes an effect of permitting the physician to intuitively comprehend the deterioration degrees of the elements according to the colors for the deterioration degrees.

Moreover, according to the fourth embodiment, the deterioration degree information may be prepared by further associating the positions of the elements with symbols according to the deterioration degrees of the respective elements. Therefore, in addition to obtaining an intuitive comprehension from the colors, the physician can clearly comprehend the deterioration degrees of the elements according to the symbols for the deterioration degrees.

Fifth Embodiment

The fifth embodiment relates to a form in which a trigger can be set for checking the ultrasound probe 101 and displaying the report. As one exemplary configuration, multiple setting items as below may be made ready for a physician to suitably select.

(a) A setting where the elements undergo checking and their deterioration degrees are displayed every time the ultrasound diagnostic apparatus is activated or started up.

(b) A setting where the elements undergo checking and their deterioration degrees are displayed at the start of each inspection of a patient.

(c) A setting where the elements undergo checking and their deterioration degrees are displayed at given intervals selected beforehand.

The intervals that can be selected in the setting may be intervals of any length discretionarily referring to a calendar, for example, a week, a month, three months, six months, or the like. As a matter of course, the selectable intervals are not limited to these, but may be of a length based on, for example, the number of days such as 10 days, 30 days, 90 days, or 180 days.

The processing circuitry 180, accordingly, includes the aforementioned setting function 184. The setting function 184 of the processing circuitry 180 is for setting, in response to an operation by an operator, a trigger for performing each of the checking function 185, the report preparing function 186, and the display controlling function 187. In one example, the setting function 184 may cause the display 103*a* to display a GUI 203 as shown in FIG. 15 for the trigger for performing each function to be set. In this case, the setting function 184 may set one of three triggers, i.e., a first trigger for performing each function every time the ultrasound diagnostic apparatus 1 is activated, a second trigger for performing each function for each ultrasound inspection of a subject P as a patient, and a third trigger for performing each function at preset intervals. Here, the setting function 184 may set the first trigger in response to, for example, an operation on a check box for "Boot up" in the GUI 203. Also, the setting function 184 may set the second trigger in response to, for example, an operation on a check box for "New patient" in the GUI 203. The setting function 184 may set the third trigger in response to, for example, an operation on any of the check boxes for "1 Week", "1 Month", "3 Months", and "6 Months" in the GUI 203.

The remaining aspects may be the same as any of the first to fourth embodiments.

With the above configuration, the processing circuitry 180 presets the first trigger, the second trigger, or the third trigger in response to an operation by the physician. Accordingly, in step ST20 of the operation flow which comes after the trigger setting, step ST21*a* is performed based on the setting, in place of step ST21 described above in which the start button operation is expected.

In step ST21*a*, the processing circuitry 180 determines whether or not to start the checking based on the setting given through the GUI 203. If the determination result here is "No", step ST20 is ended. For example, the case "No" here corresponds to an instance where "1 Week" was set through the GUI 203 but a week has not passed yet since the last checking operation. On the other hand, if the determination result in step ST21*a* indicates that the checking should be started, the operation flow proceeds to step ST22.

In step ST22, the processing circuitry 180 diagnoses the ultrasound probe 101. More specifically, the processing circuitry 180 causes ultrasound signals to be transmitted in the air and have the multiple elements of the ultrasound probe 101 receive the reflected wave signals from the air, so that the states of the elements are diagnosed based on one or more feature values of the reflected wave signals.

In step ST23, the processing circuitry 180 determines whether or not a loose connection is suspected based on the diagnosis result, and if it is determined that a loose connection is suspected, the operation flow proceeds to step ST24*a*-1. If not, the operation flow proceeds to step ST25.

In step ST24*a*-1, the processing circuitry 180 causes the display 103*a* to display the retry message Rm1 and the start button Bt1 as shown in FIG. 9. Accordingly, the ultrasound diagnostic apparatus 1 has the connection between the ultrasound probe 101 and the apparatus main body 100 checked through the action of attachment or detachment of the ultrasound probe 101 by the physician, cleaning of the probe connector, or the like.

After confirming the connection, in step ST24*a*-2, the processing circuitry 180 detects an operation by the physician on the start button Bt1, and returns to the operation in step ST22.

On the other hand, in step ST25 after step ST23, the processing circuitry 180 determines whether or not the diagnosis of the states of the elements has been completed. In one example, the determination performed by the processing circuitry 180 in step ST25 includes determining whether or not all the one or more ultrasound probes 101 connected to the apparatus main body 100 have been diagnosed for their element states. If the determination result in step ST25 is "No", the operation flow returns to step ST22 so that the diagnosis of the one or more ultrasound probes 101 is continued. If the determination result in step ST25 indicates completion of the diagnosis, the operations in step ST20 are ended. Therefore, step ST20 constituted by steps ST21 to ST25 is finished.

Subsequently, steps ST30 to ST40 are performed in a manner as described.

According to the fifth embodiment as described above, a trigger for performing each of the diagnosing process, the preparing process, and the display controlling process is set in response to an operator's operation. Thus, while providing the effects similar to the first to fourth embodiments, the fifth embodiment further realizes an effect of enabling a setting of a desired trigger so that the ultrasound probe is diagnosed and the diagnosis result is displayed upon occurrence of the set trigger.

Moreover, according to the fifth embodiment, one of the first trigger for performing each process every time the ultrasound diagnostic apparatus is activated, the second trigger for performing each process for each ultrasound inspection of a subject, and the third trigger for performing each process at preset intervals may be set. With this setting, each processing can be performed not only upon occurrence of a desired trigger but also at desired frequency according to the desired trigger.

Sixth Embodiment

The sixth embodiment may be understood as a modification of any of the first to fifth embodiments, and it relates to a form of checking the elements in the ultrasound probe 101 for the display of the deterioration degrees of the elements, right before deactivation of the ultrasound diagnostic apparatus 1. For example, as shown in the upper part of the flowchart in FIG. 17, the operation flow proceeds with step ST10 and then step ST40, followed by steps ST20 to ST30. Here, if a modification of one of the first to fourth embodiments is assumed, the processing circuitry 180 detects an operation on an end button instead of an operation on a start button in step ST21, and then performs the operations in steps ST22 to ST25 and ST30 in response to detecting the operation on the end button. If, on the other hand, a modification of the fifth embodiment is assumed for the upper part of the flowchart in FIG. 17, the processing circuitry 180 with the setting function 184 may enable, in addition to the first to third triggers, a setting of a fourth trigger for performing each of the checking function 185, the report preparing function 186, and the display controlling function 187 every time the ultrasound diagnostic apparatus 1 is to be deactivated. In another exemplary configuration, the processing circuitry 180 with the setting function 184 may permit this fourth trigger for performing each function right before every deactivation of the ultrasound diagnostic apparatus 1 to be set in place of the first trigger.

The remaining aspects may be the same as any of the first to fifth embodiments.

With the above configuration, steps ST20 to ST30 are performed after steps ST10 and ST40 as shown in the upper part of the flowchart in FIG. 17. Accordingly, on the day of diagnosis of the ultrasound probe 101, the elements in the ultrasound probe 101 are checked right before deactivation of the ultrasound diagnostic apparatus 1 and the probe diagnosis report 200 is displayed to show the deterioration degrees of the elements. This display corresponds to the preview display in step ST34. Upon completion of the operations in step ST30, the ultrasound diagnostic apparatus 1 is deactivated.

On the day next to the day of diagnosis of the ultrasound probe 101, step ST10 is performed where the ultrasound diagnostic apparatus 1 is activated, as shown in the lower part of the flowchart in FIG. 17. After step ST10, step ST40 is performed where the processing circuitry 180 superimposes the latest probe diagnosis report 200 onto the ultrasound image of a subject P and causes the display 103a to display the resultant image. In step ST40, the processing circuitry 180 may also superimpose the latest second image 202 onto the ultrasound image of the subject P for display on the display 103a. As such, if step ST40 is performed on the day next to the day of diagnosis of the ultrasound probe 101, the latest probe diagnosis report 200 and the latest second image 202 are based on the check result obtained on the previous day. In accordance with the completion of step ST40, the ultrasound diagnostic apparatus 1 terminates the ultrasound inspection of the subject P. When there are other subjects P, the operations in step ST40 are similarly performed for them.

Upon finishing the operations in step ST40 for all the subjects P, steps ST20 to ST30 are performed in the manner as discussed.

According to the sixth embodiment as described above, the diagnosing process and the preparing process can be performed every time the ultrasound diagnostic apparatus 1 is to be deactivated. Thus, while providing the effects similar to the first to fifth embodiments, the sixth embodiment can further meet the demand of a physician who desires to avoid a probe check at the activation (e.g., in the morning), by performing the probe check at the deactivation (e.g., in the night).

According to at least one of the foregoing embodiments, physicians, etc. can comprehend the deterioration, defects, and so on of the elements in an ultrasound probe during the ongoing ultrasound inspection of a subject.

The term "processor" used herein refers to, for example, a central processing unit (CPU) or a graphics processing unit (GPU), or various types of circuitry which may be an application-specific integrated circuit (ASIC), a programmable logic device (such as a simple programmable logic device (SPLD), a complex programmable logic device (CPLD), or a field programmable gate array (EPGA)), and so on. The processor reads programs stored in the memory and executes them to realize corresponding functions. The programs may be incorporated directly in circuits of the processor, instead of being stored in the memory. According to such implementation, the processor reads the programs incorporated in its circuits and executes them to realize the functions. The embodiments herein do not limit each processor to a single circuitry-type processor. Multiple independent circuits may be combined and integrated as one processor to realize the intended functions. Furthermore, multiple components or features as given in FIG. 1 may be integrated as one processor to realize their respective functions.

While certain embodiments have been described, these embodiments have been presented by way of example only, and are not intended to limit the scope of the inventions.

Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasound diagnostic apparatus connectable with an ultrasound probe which comprises a plurality of elements configured to transmit an ultrasound signal and to receive a reflected wave signal from a subject or from air, wherein the ultrasound diagnostic apparatus comprises:
processing circuitry configured to:
generate an ultrasound image based on an output of the plurality of elements of the ultrasound probe;
diagnose states of the plurality of elements of the ultrasound probe based on a feature value of the reflected wave signal received by the ultrasound probe;
generate, based on the diagnosed states of the plurality of elements, a plurality of types of deterioration degree information indicative of deterioration degrees of the plurality of elements, for respective groups of elements that constitute the plurality of elements; and
superimpose the plurality of types of deterioration degree information onto the ultrasound image of the subject in such a manner that each of the plurality of types of deterioration degree information is recognizable;
superimpose a second image, which is an image corresponding to one of the plurality of types of deterioration degree information and involving a deterioration degree larger than a threshold, onto the ultrasound image of the subject in such a manner that the second image covers a region that is based on an output of elements with the deterioration degree larger than the threshold; and
in response to scan conditions for the ultrasound image being changed according to an operation by an operator, add a correction to the second image based on the changed scan conditions and a number of elements that form a display target image among the ultrasound image, to superimpose the corrected second image onto the display target image,
wherein a ratio rA of a number of elements forming the second image after the correction to a number of elements forming the second image before the correction is smaller than a ratio rB of a number of elements forming the ultrasound image after the correction to a number of elements forming the ultrasound image before the correction (rA<rB); and
to cause a display to display a resultant image.

2. The ultrasound diagnostic apparatus according to claim 1, wherein the processing circuitry is further configured to prepare the plurality of types of deterioration degree information in a form of a probe diagnosis report comprising a first image and identification information of the ultrasound probe, the first image being prepared by associating positions of the elements in the ultrasound probe with the deterioration degrees of the plurality of elements.

3. The ultrasound diagnostic apparatus according to claim 1, wherein the processing circuitry is further configured to correct the plurality of types of deterioration degree information based on scan conditions for the ultrasound image of the subject and also on a number of the plurality of elements that form an image of a display target among the ultrasound image of the subject, to superimpose the corrected plurality of types of deterioration degree information onto the image of the display target, and to cause the display to display the resultant image.

4. The ultrasound diagnostic apparatus according to claim 1, wherein the processing circuitry is further configured to prepare the plurality of types of deterioration degree information by grouping the elements into a number of groups fewer than a number of the plurality of elements, based on positions of the plurality of elements, and associating the plurality of types of deterioration degrees with the groups, respectively.

5. The ultrasound diagnostic apparatus according to claim 1, wherein the processing circuitry is further configured to prepare the plurality of types of deterioration degree information by individually associating positions of the plurality of elements with a plurality of colors according to the plurality of types of deterioration degrees of the plurality of elements.

6. The ultrasound diagnostic apparatus according to claim 5, wherein the processing circuitry is further configured to prepare the plurality of types of deterioration degree information by further associating the positions of the plurality of elements with symbols according to the plurality of types of deterioration degrees of the elements.

7. The ultrasound diagnostic apparatus according to claim 1, wherein the processing circuitry is further configured to set, in response to an operation by an operator, a trigger for performing a process including the diagnosing, the preparing, and the superimposing.

8. The ultrasound diagnostic apparatus according to claim 7, wherein the processing circuitry is further configured to set, as the trigger, in response to the operation by the operator, one of (1) a first trigger, which triggers performance of the process every time the ultrasound diagnostic apparatus is activated, (2) a second trigger, which triggers performance of the process for an ultrasound inspection of the subject, and (3) a third trigger, which triggers performance of the process at preset intervals.

9. An ultrasound probe diagnosing method performed by an ultrasound diagnostic apparatus connectable with an ultrasound probe, which comprises a plurality of elements configured to transmit an ultrasound signal and to receive a reflected wave signal from a subject or from air, the ultrasound diagnostic apparatus configured to generate an ultrasound image based on an output of the plurality of elements, wherein the ultrasound probe diagnosing method comprises:
diagnosing states of the plurality of elements of the ultrasound probe based on a feature value of the reflected wave signal received by the ultrasound probe;
generating, based on the diagnosed states of the plurality of elements, a plurality of types of deterioration degree information indicative of deterioration degrees of the plurality of elements, for respective groups of elements that constitute the plurality of elements; and
superimposing the plurality of types of deterioration degree information onto the ultrasound image of the subject in such a manner that each of the plurality of types of deterioration degree information is recognizable;
superimposing a second image, which is an image corresponding to one of the plurality of types of deterioration degree information and involving a deterioration degree larger than a threshold, onto the ultrasound image of the subject in such a manner that the second image covers a region that is based on an output of elements with the deterioration degree larger than the threshold; and in response to scan conditions for the ultrasound image being changed according to an operation by an operator, correcting the second image based on the changed scan conditions and a number of elements that form a display target image among the ultrasound image, and superimposing the corrected second image onto the display target image, wherein a ratio rA of a number of elements forming the second image after the correction to a number of elements forming the second image before the correction is smaller than a ratio rB of a number of elements forming the ultrasound image after the correction to a number of elements forming the ultrasound image before the correction (rA<rB); and causing a display to display a resultant image.

10. The ultrasound diagnostic apparatus of claim 1, further comprising a memory storing predetermined feature data, wherein the processing circuitry is further configured to diagnose the states of the plurality of elements by reading the predetermined feature data from the memory and comparing the predetermined feature data to the feature value of the reflected wave signal.

11. The ultrasound diagnostic apparatus according to claim 1, wherein the processing circuitry is further configured to cause the display to use a plurality of colors for displaying the plurality of types of deterioration degree information, respectively.

12. The ultrasound diagnostic apparatus according to claim 1, wherein the deterioration degree information comprises a deterioration degree of the grouped elements and information on an expected influence on image diagnosis.

13. The ultrasound diagnostic apparatus according to claim 1, wherein the deterioration degree information comprises a deterioration degree of the grouped elements and availability for image diagnosis.

14. The ultrasound diagnostic apparatus according to claim 1, wherein the second image is semitransparent so that the ultrasound image is seen in pale colors through the second image, transparency of the second image being set according to the deterioration degrees.

15. The ultrasound diagnostic apparatus according to claim 2, wherein the processing circuitry is further configured to generate a second image for covering a region that is based on an output of elements with a deterioration degree larger than a threshold, to superimpose the probe diagnosis report or the second image onto the ultrasound image according to an operation by an operator, and to cause the display to display the resultant image.

* * * * *